(12) United States Patent
Parrington et al.

(10) Patent No.: US 8,236,776 B2
(45) Date of Patent: Aug. 7, 2012

(54) MODIFIED CEA NUCLEIC ACID AND EXPRESSION VECTORS

(75) Inventors: Mark Parrington, Bradford (CA); Linong Zhang, Concord (CA); Benjamin Rovinski, Thornhill (CA); Linda R. Gritz, Somerville, MA (US); Patricia Greenhalgh, Bedford, MA (US)

(73) Assignee: Sanofi Pasteur Limited, Toronto, Ontario (CA)

( * ) Notice: Subject to any disclaimer, the term of this patent is extended or adjusted under 35 U.S.C. 154(b) by 228 days.

(21) Appl. No.: 12/716,239

(22) Filed: Mar. 2, 2010

(65) Prior Publication Data

US 2010/0285065 A1     Nov. 11, 2010

Related U.S. Application Data

(62) Division of application No. 10/510,677, filed as application No. PCT/US03/10916 on Apr. 9, 2003, now Pat. No. 7,786,278.

(60) Provisional application No. 60/370,972, filed on Apr. 9, 2002.

(51) Int. Cl.
*A61K 48/00* (2006.01)
(52) U.S. Cl. .................................................. 514/44 R
(58) Field of Classification Search ................. 514/44 R
See application file for complete search history.

*Primary Examiner* — Anne Marie S Wehbe
(74) *Attorney, Agent, or Firm* — Patrick J. Halloran; Reza Yacoob

(57) ABSTRACT

The present invention relates to a nucleic acid encoding a polypeptide and the use of the nucleic acid or polypeptide in preventing and/or treating cancer. The invention relates to improved vectors for the insertion and expression of foreign genes encoding tumor antigens for use in immunotherapeutic treatment of cancer. One such foreign DNA sequence is modified CEA nucleic acid.

18 Claims, 14 Drawing Sheets

FIGURE 1
A.
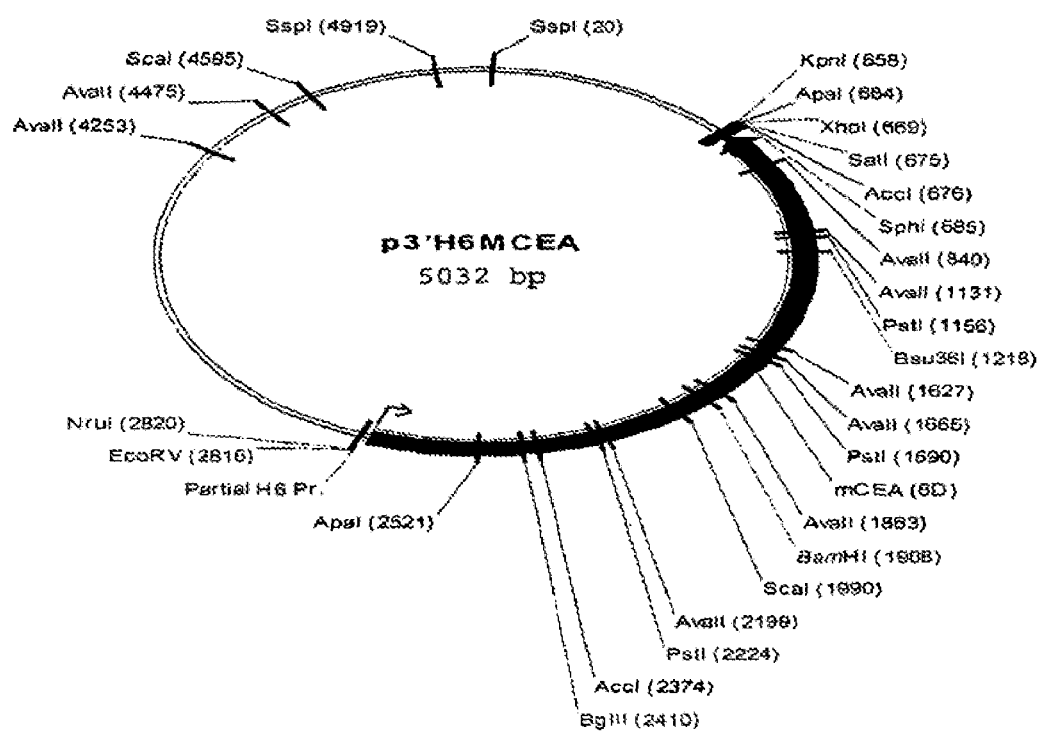
B.
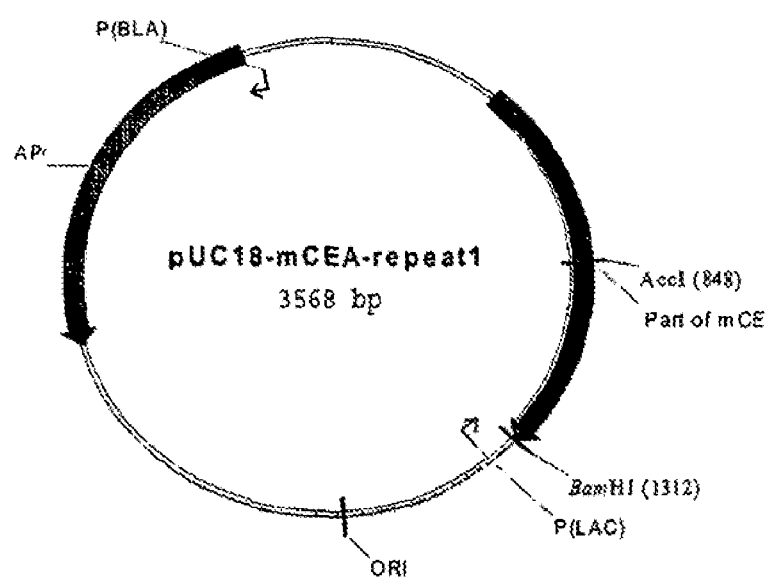

pUC18 mCEA modified repeat 2 (gsoe)

pUC18 mCEA modified repeat 2 gsoe minus Ala

FIGURE 9A

```
               1                                                        50
    mCEA(6D)   ATGGAGTCTC CCTCGGCCCC TCCCCACAGA TGGTGCATCC CCTGGCAGAG
mCEA(6D,1st&2nd) ATGGAGTCTC CCTCGGCCCC TCCCCACAGA TGGTGCATCC CCTGGCAGAG 51                                                       100
    mCEA(6D)   GCTCCTGCTC ACAGCCTCAC TTCTAACCTT CTGGAACCCG CCCACCACTG
mCEA(6D,1st&2nd) GCTCCTGCTC ACAGCCTCAC TTCTAACCTT CTGGAACCCG CCCACCACTG 101                                                      150
    mCEA(6D)   CCAAGCTCAC TATTGAATCC ACGCCGTTCA ATGTCGCAGA GGGGAAGGAG
mCEA(6D,1st&2nd) CCAAGCTCAC TATTGAATCC ACGCCGTTCA ATGTCGCAGA GGGGAAGGAG 151                                                      200
    mCEA(6D)   GTGCTTCTAC TTGTCCACAA TCTGCCCCAG CATCTTTTTG GCTACAGCTG
mCEA(6D,1st&2nd) GTGCTTCTAC TTGTCCACAA TCTGCCCCAG CATCTTTTTG GCTACAGCTG 201                                                      250
    mCEA(6D)   GTACAAAGGT GAAAGAGTGG ATGGCAACCG TCAAATTATA GGATATGTAA
mCEA(6D,1st&2nd) GTACAAAGGT GAAAGAGTGG ATGGCAACCG TCAAATTATA GGATATGTAA 251                                                      300
    mCEA(6D)   TAGGAACTCA ACAAGCTACC CCAGGGCCCG CATACAGTGG TCGAGAGATA
mCEA(6D,1st&2nd) TAGGAACTCA ACAAGCTACC CCAGGGCCCG CATACAGTGG TCGAGAGATA 301                                                      350
    mCEA(6D)   ATATACCCCA ATGCATCCCT GCTGATCCAG AACATCATCC AGAATGACAC
mCEA(6D,1st&2nd) ATATACCCCA ATGCATCCCT GCTGATCCAG AACATCATCC AGAATGACAC 351                                                      400
    mCEA(6D)   AGGATTCTAC ACCCTACACG TCATAAAGTC AGATCTTGTG AATGAAGAAG
mCEA(6D,1st&2nd) AGGATTCTAC ACCCTACACG TCATAAAGTC AGATCTTGTG AATGAAGAAG 401                                                      450
    mCEA(6D)   CAACTGGCCA GTTCCGGGTA TACCCGGAGC TGCCCAAGCC CTCCATCTCC
mCEA(6D,1st&2nd) CAACTGGCCA GTTCCGGGTA TACCCGGAAC TCCCTAAGCC TTCTATTAGC 451                                                      500
    mCEA(6D)   AGCAACAACT CCAAACCCGT GGAGGACAAG GATGCTGTGG CCTTCACCTG
mCEA(6D,1st&2nd) TCCAATAATA GTAAGCCTGT CGAAGACAAA GATGCCGTCG CTTTTACATG 501                                                      550
    mCEA(6D)   TGAACCTGAG ACTCAGGACG CAACCTACCT GTGGTGGGTA AACAATCAGA
mCEA(6D,1st&2nd) CGAGCCCGAA ACTCAAGACG CAACATATCT CTGGTGGGTG AACAACCAGT 551                                                      600
    mCEA(6D)   GCCTCCCGGT CAGTCCCAGG CTGCAGCTGT CCAATGGCAA CAGGACCCTC
mCEA(6D,1st&2nd) CCCTGCCTGT GTCCCCTAGA CTCCAACTCA GCAACGGAAA TAGAACTCTG 601                                                      650
    mCEA(6D)   ACTCTATTCA ATGTCACAAG AAATGACACA GCAAGCTACA AATGTGAAAC
mCEA(6D,1st&2nd) ACCCTGTTTA ACGTGACCAG GAACGACACA GCAAGCTACA AATGCGAAAC
```

FIGURE 9B

```
                       661                                                           700
          mCEA(6D)     CCAGAACCCA GTGAGTGCCA GGCGCAGTGA TTCAGTCATC CTGAATGTCC
mCEA(6D,1st&2nd)       CCAAAATCCA GTCAGCGCCA GGAGGTCTGA TTCAGTGATT CTCAACGTGC 701                                                           750
          mCEA(6D)     TCTATGGCCC GGATGCCCCC ACCATTTCCC CTCTAAACAC ATCTTACAGA
mCEA(6D,1st&2nd)       TTTACGGACC CGATGCTCCT ACAATCAGCC CTCTAAACAC AAGCTATAGA 751                                                           800
          mCEA(6D)     TCAGGGGAAA ATCTGAACCT CTCCTGCCAC GCAGCCTCTA ACCCACCTGC
mCEA(6D,1st&2nd)       TCAGGGGAAA ATCTGAATCT GAGCTGTCAT GCCGCTAGCA ATCCTCCCGC 801                                                           850
          mCEA(6D)     ACAGTACTCT TGGTTTGTCA ATGGGACTTT CCAGCAATCC ACCCAAGAGC
mCEA(6D,1st&2nd)       CCAATACAGC TGGTTTGTCA ATGGCACTTT CCAACAGTCC ACCCAGGAAC 851                                                           900
          mCEA(6D)     TCTTTATCCC CAACATCACT GTGAATAATA GTGGATCCTA TACGTGCCAA
mCEA(6D,1st&2nd)       TGTTCATTCC CAATATTACC GTGAACAATA GTGGATCCTA CACGTGCCAA 901                                                           950
          mCEA(6D)     GCCCATAACT CAGACACTGG CCTCAATAGG ACCACAGTCA CGACGATCAC
mCEA(6D,1st&2nd)       GCTCACAATA GCGACACCGG ACTCAACCGC ACAACCGTGA CGACGATTAC 951                                                          1000
          mCEA(6D)     AGTCTATGAG CCACCCAAAC CCTTCATCAC CAGCAACAAC TCCAACCCCG
mCEA(6D,1st&2nd)       CGTGTATGAG CCACCAAAAC CATTCATAAC TAGTAACAAT TCTAACCCAG 1001                                                         1050
          mCEA(6D)     TGGAGGATGA GGATGCTGTA GCCTTAACCT GTGAACCTGA GATTCAGAAC
mCEA(6D,1st&2nd)       TTGAGGATGA GGACGCAGTT GCATTAACTT GTGAGCCAGA GATTCAAAAT 1051                                                         1100
          mCEA(6D)     ACAACCTACC TGTGGTGGGT AAATAATCAG AGCCTCCCGG TCAGTCCCAG
mCEA(6D,1st&2nd)       ACCACTTATT TATGGTGGGT CAATAACCAA AGTTTGCCGG TTAGCCCACG 1101                                                         1150
          mCEA(6D)     GCTGCAGCTG TCCAATGACA ACAGGACCCT CACTCTACTC AGTGTCACAA
mCEA(6D,1st&2nd)       CTTGCAGTTG TCTAATGATA ACCGCACATT GACACTCCTG TCCGTTACTC 1151                                                         1200
          mCEA(6D)     GGAATGATGT AGGACCCTAT GAGTGTGGAA TCCAGAACGA ATTAAGTGTT
mCEA(6D,1st&2nd)       GCAATGATGT AGGACCTTAT GAGTGTGGCA TTCAGAATGA ATTATCCGTT 1201                                                         1250
          mCEA(6D)     GACCACAGCG ACCCAGTCAT CCTGAATGTC CTCTATGGCC CAGACGACCC
mCEA(6D,1st&2nd)       GATCACTCCG ACCCTGTTAT CCTTAATGTT TTGTATGGCC CAGACGACCC 1251                                                         1300
          mCEA(6D)     CACCATTTCC CCCTCATACA CCTATTACCG TCCAGGGGTG AACCTCAGCC
mCEA(6D,1st&2nd)       AACTATATCT CCATCATACA CCTACTACCG TCCCGGCGTG AACTTGAGCC
```

FIGURE 9C

```
                        1301                                                      1350
            mCEA(6D)    TCTCCTGCCA TGCAGCCTCT AACCCACCTG CACAGTATTC TTGGCTGATT
    mCEA(6D,1st&2nd)    TTTCTTGCCA TGCAGCATCC AACCCCCCTG CACAGTACTC CTGGCTGATT 1351                                                      1400
            mCEA(6D)    GATGGGAACA TCCAGCAACA CACACAAGAG CTCTTTATCT CCAACATCAC
    mCEA(6D,1st&2nd)    GATGGAAACA TTCAGCAGCA TACTCAAGAG TTATTTATAA GCAACATAAC 1401                                                      1450
            mCEA(6D)    TGAGAAGAAC AGCGGACTCT ATCCTGCCA GGCCAATAAC TCAGCCAGTG
    mCEA(6D,1st&2nd)    TGAGAAGAAC AGCGGACTCT ATACTTGCCA GGCCAATAAC TCAGCCAGTG 1451                                                      1500
            mCEA(6D)    GCCACAGCAG GACTACAGTC AAGACAATCA CAGTCTCTGC GGAGCTGCCC
    mCEA(6D,1st&2nd)    GTCACAGCAG GACTACAGTT AAAACAATAA CTGTTTCCGC GGAGCTGCCC 1501                                                      1550
            mCEA(6D)    AAGCCCTCCA TCTCCAGCAA CAACTCCAAA CCCGTGGAGG ACAAGGATGC
    mCEA(6D,1st&2nd)    AAGCCCTCCA TCTCCAGCAA CAACTCCAAA CCCGTGGAGG ACAAGGATGC 1551                                                      1600
            mCEA(6D)    TGTGGCCTTC ACCTGTGAAC CTGAGGCTCA GAACACAACC TACCTGTGGT
    mCEA(6D,1st&2nd)    TGTGGCCTTC ACCTGTGAAC CTGAGGCTCA GAACACAACC TACCTGTGGT 1601                                                      1650
            mCEA(6D)    GGGTAAATGG TCAGAGCCTC CCAGTCAGTC CCAGGCTGCA GCTGTCCAAT
    mCEA(6D,1st&2nd)    GGGTAAATGG TCAGAGCCTC CCAGTCAGTC CCAGGCTGCA GCTGTCCAAT 1651                                                      1700
            mCEA(6D)    GGCAACAGGA CCCTCACTCT ATTCAATGTC ACAAGAAATG ACGCAAGAGC
    mCEA(6D,1st&2nd)    GGCAACAGGA CCCTCACTCT ATTCAATGTC ACAAGAAATG ACGCAAGAGC 1701                                                      1750
            mCEA(6D)    CTATGTATGT GGAATCCAGA ACTCAGTGAG TGCAAACCGC AGTGACCCAG
    mCEA(6D,1st&2nd)    CTATGTATGT GGAATCCAGA ACTCAGTGAG TGCAAACCGC AGTGACCCAG 1751                                                      1800
            mCEA(6D)    TCACCCTGGA TGTCCTCTAT GGGCCGGACA CCCCCATCAT TTCCCCCCCA
    mCEA(6D,1st&2nd)    TCACCCTGGA TGTCCTCTAT GGGCCGGACA CCCCCATCAT TTCCCCCCCA 1801                                                      1850
            mCEA(6D)    GACTCGTCTT ACCTTTCGGG AGCGGACCTC AACCTCTCCT GCCACTCGGC
    mCEA(6D,1st&2nd)    GACTCGTCTT ACCTTTCGGG AGCGGACCTC AACCTCTCCT GCCACTCGGC 1851                                                      1900
            mCEA(6D)    CTCTAACCCA TCCCCGCAGT ATTCTTGGCG TATCAATGGG ATACCGCAGC
    mCEA(6D,1st&2nd)    CTCTAACCCA TCCCCGCAGT ATTCTTGGCG TATCAATGGG ATACCGCAGC 1901                                                      1950
            mCEA(6D)    AACACACACA AGTTCTCTTT ATCGCCAAAA TCACGCCAAA TAATAACGGG
    mCEA(6D,1st&2nd)    AACACACACA AGTTCTCTTT ATCGCCAAAA TCACGCCAAA TAATAACGGG
```

FIGURE 9D

```
                        1951                                                    2000
        mCEA(6D)        ACCTATGCCT GTTTTGTCTC TAACTTGGCT ACTGGCCGCA ATAATTCCAT
mCEA(6D,1st&2nd)        ACCTATGCCT GTTTTGTCTC TAACTTGGCT ACTGGCCGCA ATAATTCCAT 2001                                                    2050
        mCEA(6D)        AGTCAAGAGC ATCACAGTCT CTGCATCTGG AACTTCTCCT GGTCTCTCAG
mCEA(6D,1st&2nd)        AGTCAAGAGC ATCACAGTCT CTGCATCTGG AACTTCTCCT GGTCTCTCAG 2051                                                    2100
        mCEA(6D)        CTGGGGCCAC TGTCGGCATC ATGATTGGAG TGCTGGTTGG GGTTGCTCTG
mCEA(6D,1st&2nd)        CTGGGGCCAC TGTCGGCATC ATGATTGGAG TGCTGGTTGG GGTTGCTCTG 2101
        mCEA(6D)        ATATAG
mCEA(6D,1st&2nd)        ATATAG
```

MODIFIED CEA NUCLEIC ACID AND EXPRESSION VECTORS

RELATED APPLICATIONS

This application is a divisional application of U.S. Ser. No 10/510,677 filed Oct. 6, 2004, now U.S. Pat. No. 7,786,278 B2, which is the National Stage Application under 35 U.S.C. §371 of International Application No. PCT/US03/10916 filed Apr. 9, 2003, which claims priority to U.S. Provisional Application No. 60/370,972 filed Apr. 9, 2002.

FIELD OF THE INVENTION

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

BACKGROUND OF THE INVENTION

There has been tremendous increase in last few years in the development of cancer vaccines with Tumour-associated antigens (TAAs) due to the great advances in identification of molecules based on the expression profiling on primary tumours and normal cells with the help of several techniques such as high density microarray, SEREX, immunohistochemistry (IHC), RT-PCR, in-situ hybridization (ISH) and laser capture microscopy (Rosenberg, Immunity, 1999; Sgroi et al, 1999, Schena et al, 1995, Offringa et al, 2000). The TAAs are antigens expressed or over-expressed by tumour cells and could be specific to one or several tumours for example CEA antigen is expressed in colorectal, breast and lung cancers. Sgroi et al (1999) identified several genes differentially expressed in invasive and metastatic carcinoma cells with combined use of laser capture microdissection and cDNA microarrays. Several delivery systems like DNA or viruses could be used for therapeutic vaccination against human cancers (Bonnet et al, 2000) and can elicit immune responses and also break immune tolerance against TAAs. Tumour cells can be rendered more immunogenic by inserting transgenes encoding T cell co-stimulatory molecules such as B7.1 or cytokines IFNgamma, IL2, GM-CSF etc. Co-expression of a TAA and a cytokine or a co-stimulatory molecule can develop effective therapeutic vaccine (Hodge et al, 95, Bronte et al, 1995, Chamberlain et al, 1996).

There is a need in the art for reagents and methodologies useful in stimulating an immune response to prevent or treat cancers. The present inventions provides such reagents and methodologies which overcome many of the difficulties encountered by others in attempting to treat cancers such as cancer. In particular, the present invention provides a novel coding sequence for CEA. This nucleotide sequence, CEA (6D)-1,2, includes sequence modifications that eliminate the expression of truncated forms of CEA as expressed from expression vectors. Such a modified sequence is desired by those of skill in the art to improve expression and immunization protocols for CEA.

SUMMARY OF THE INVENTION

The present invention provides an immunogenic target for administration to a patient to prevent and/or treat cancer. In particular, the immunogenic target is a CEA tumor antigen ("TA") and/or an angiogenesis-associated antigen ("AA"). In one embodiment, the immunogenic target is encoded by a modified CEA nucleotide sequence (CEA(6D)-1,2) that improves CEA expression in transfected cells. In certain embodiments, the TA and/or AA are administered to a patient as a nucleic acid contained within a plasmid or other delivery vector, such as a recombinant virus. The TA and/or AA may also be administered in combination with an immune stimulator, such as a co-stimulatory molecule or adjuvant.

BRIEF DESCRIPTION OF THE DRAWINGS

FIG. 1. A. Illustration of plasmid p3'H6MCEA comprising the CEA coding sequence with the 6D modification under the control of partial H6 promoter. B. Illustration of plasmid pSE1544.9 (pUC18-mCEA repeat 1).

FIG. 9A-D. Comparison of nucleotide sequence of CAP (6D) (SEQ ID NO:23) and CAP(6D)-1,2 (SEQ ID NO:28). Differences between the sequences are underlined.

DETAILED DESCRIPTION

Figure 2:
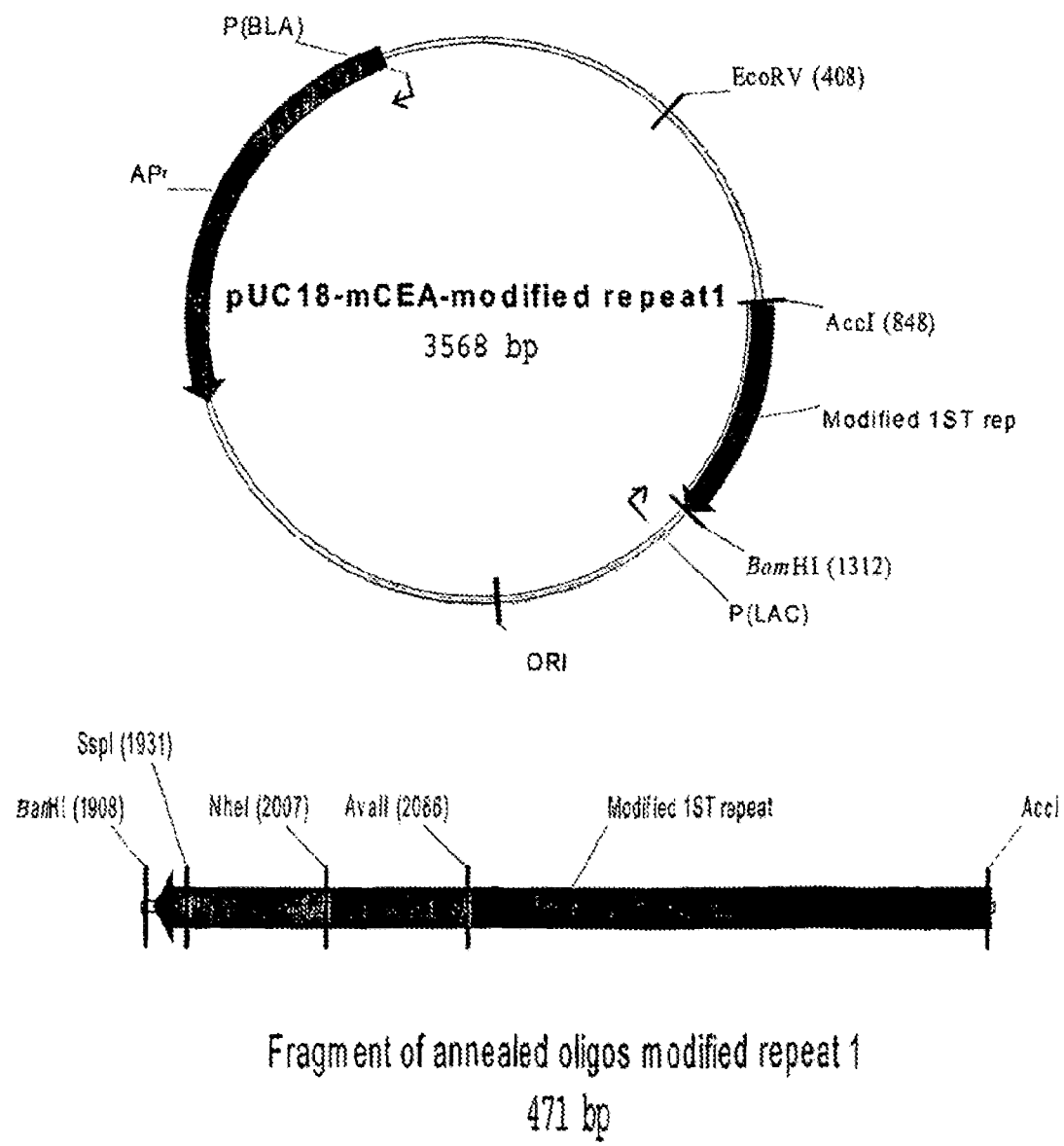
FIG. 2. Illustration of plasmid pSEI 616.44 (pUC18-mCEA-modified repeat 1).

The present invention provides reagents and methodologies useful for treating and/or preventing cancer. All references cited within this application are incorporated by reference.

In one embodiment, the present invention relates to the induction or enhancement of an immune response against one or more tumor antigens ("TA") to prevent and/or treat cancer. In certain embodiments, one or more TAs may be combined. In preferred embodiments, the immune response results from expression of a TA in a host cell following administration of a nucleic acid vector encoding the tumor antigen or the tumor antigen itself in the form of a peptide or polypeptide, for example.

As used herein, an "antigen" is a molecule (such as a polypeptide) or a portion thereof that produces an immune response in a host to whom the antigen has been administered. The immune response may include the production of antibodies that bind to at least one epitope of the antigen and/or the generation of a cellular immune response against cells expressing an epitope of the antigen. The response may be an enhancement of a current immune response by, for example, causing increased antibody production, production of antibodies with increased affinity for the antigen, or an increased cellular response (i.e., increased T cells). An antigen that produces an immune response may alternatively be referred to as being immunogenic or as an immunogen. In describing the present invention, a TA may be referred to as an "immunogenic target".

TA includes both tumor-associated antigens (TAAs) and tumor-specific antigens (TSAs), where a cancerous cell is the source of the antigen. A TAA is an antigen that is expressed on the surface of a tumor cell in higher amounts than is observed on normal cells or an antigen that is expressed on normal cells during fetal development. A TSA is an antigen that is unique to tumor cells and is not expressed on normal cells. TA further includes TAAs or TSAs, antigenic fragments thereof, and modified versions that retain their antigenicity.

TAs are typically classified into five categories according to their expression pattern, function, or genetic origin: cancer-testis (CT) antigens (i.e., MAGE, NY-ESO-1); melanocyte differentiation antigens (i.e., Melan A/MART-1, tyrosinase, gp100); mutational antigens (i.e., MUM-1, p53, CDK-4); overexpressed 'self' antigens (i.e., HER-2/neu, p53); and, viral antigens (i.e., HPV, EBV). For the purposes of practicing the present invention, a suitable TA is any TA that induces or enhances an anti-tumor immune response in a host to whom the TA has been administered. Suitable TAs include, for example, gp100 (Cox et al., Science, 264:716-719 (1994)), MART-1/Melan A (Kawakami et al., J. Exp. Med., 180:347-352 (1994)), gp75 (TRP-1) (Wang et al., J. Exp. Med., 186:1131-1140 (1996)), tyrosinase (Wolfel et al., Eur. J. Immunol., 24:759-764 (1994); WO 200175117; WO 200175016; WO 200175007), NY-ESO-1 (WO 98/14464; WO 99/18206), melanoma proteoglycan (Hellstrom et al., J. Immunol., 130:1467-1472 (1983)), MAGE family antigens (i.e., MAGE-1, 2,3,4,6,12, 51; Van der Bruggen et al., Science, 254:1643-1647 (1991); U.S. Pat. No. 6,235,525; CN 1319611), BAGE family antigens (Boel et al., Immunity, 2:167-175 (1995)), GAGE family antigens (i.e., GAGE-1,2; Van den Eynde et al., J. Exp. Med., 182:689-698 (1995); U.S. Pat. No. 6,013,765), RAGE family antigens (i.e., RAGE-1; Gaugler et at., Immunogenetics, 44:323-330 (1996); U.S. Pat. No. 5,939,526), N-acetylglucosaminyltransferase-V (Guilloux et at., J. Exp. Med., 183:1173-1183 (1996)), p15 (Robbins et al., J. Immunol. 154:5944-5950 (1995)), β-catenin (Robbins et al., J. Exp. Med., 183:1185-1192 (1996)), MUM-1 (Coulie et al., Proc. Natl. Acad. Sci. USA, 92:7976-7980 (1995)), cyclin dependent kinase-4 (CDK4) (Wolfe) et al., Science, 269:1281-1284 (1995)), p21-ras (Fossum et at., Int. J. Cancer, 56:40-45 (1994)), BCR-abl (Bocchia et al., Blood, 85:2680-2684 (1995)), p53 (Theobald et al., Proc. Natl. Acad. Sci. USA, 92:11993-11997 (1995)), p185 HER2/neu (erb-B1; Fisk et al., J. Exp. Med., 181:2109-2117 (1995)), epidermal growth factor receptor (EGFR) (Harris et al., Breast Cancer Res. Treat, 29:1-2 (1994)), carcinoembryonic antigens (CEA) (Kwong et al., J. Natl. Cancer Inst., 85:982-990 (1995) U.S. Pat. Nos. 5,756,103; 5,274,087; 5,571,710; 6,071,716; 5,698,530; 6,045,802; EP 263933; EP 346710; and, EP 784483); carcinoma-associated mutated mucins (i.e., MUC-1 gene products; Jerome et al., J. Immunol., 151:1654-1662 (1993)); EBNA gene products of EBV (i.e., EBNA-1; Rickinson et al., Cancer Surveys, 13:53-80 (1992)); E7, E6 proteins of human papillomavirus (Ressing et al., J. Immunol, 154:5934-5943 (1995)); prostate specific antigen (PSA; Xue et al., The Prostate, 30:73-78 (1997)); prostate specific membrane antigen (PSMA; Israeli, et al., Cancer Res., 54:1807-1811 (1994)); idiotypic epitopes or antigens, for example, immunoglobulin idiotypes or T cell receptor idiotypes (Chen et al., J. Immunol., 153:4775-4787 (1994)); KSA (U.S. Pat. No. 5,348,887), kinesin 2 (Dietz, et al. Biochem Biophys Res Commun 2000 Sep. 7; 275(3):731-8), HIP-55, TGFβ-1 anti-apoptotic factor (Toomey, et al. Br J Biomed Sci 2001; 58(3): 177-83), tumor protein D52 (Bryne J. A., et al., Genomics, 35:523-532 (1996)), HIFT, NY-BR-1 (WO 01/47959), NY-BR-62, NY-BR-75, NY-BR-85, NY-BR-87, NY-BR-96 (Scanlan, M. Serologic and Bioinformatic Approaches to the Identification of Human Tumor Antigens, in Cancer Vaccines 2000, Cancer Research Institute, New York, N.Y.), AAC2-1, or AAC2-2, including "wild-type" (i.e., normally encoded by the genome, naturally-occurring), modified, and mutated versions as well as other fragments and derivatives thereof. Any of these TAs may be utilized alone or in combination with one another in a co-immunization protocol.

In certain cases, it may be beneficial to co-immunize patients with both TA and other antigens, such as angiogenesis-associated antigens ("AA"). An AA is an immunogenic molecule (i.e., peptide, polypeptide) associated with cells involved in the induction and/or continued development of blood vessels. For example, an AA may be expressed on an endothelial cell ("EC"), which is a primary structural component of blood vessels. Where the cancer is cancer, it is preferred that that the AA be found within or near blood vessels that supply a tumor. Immunization of a patient against an AA preferably results in an anti-AA immune response whereby angiogenic processes that occur near or within tumors are prevented and/or inhibited.

Exemplary AAs include, for example, vascular endothelial growth factor (i.e., VEGF; Bernardi, et al. J. Urol., 2001, 166(4): 1275-9; Starnes, et al. J. Thorac. Cardiovasc. Surg., 2001, 122(3): 518-23), the VEGF receptor (i.e., VEGF-R, flk-1/KDR; Starnes, et al. J. Thorac. Cardiovasc. Surg., 2001, 122(3): 518-23), EPH receptors (i.e., EPHA2; Gerety, et al. 1999, Cell, 4: 403-414), epidermal growth factor receptor (i.e., EGFR; Ciardeillo, et al. Clin. Cancer Res., 2001, 7(10): 2958-70), basic fibroblast growth factor (i.e., bFGF; Davidson, et al. Clin. Exp. Metastasis 2000, 18(6): 501-7; Poon, et al. Am J. Surg., 2001, 182(3):298-304), platelet-derived cell growth factor (i.e., PDGF-B), platelet-derived endothelial cell growth factor (PD-ECGF; Hong, et al. J. Mol. Med., 2001, 8(2):141-8), transforming growth factors (i.e., TGF-α; Hong, et al. J. Mol. Med., 2001, 8(2):141-8), endoglin (Balza, et al. Int. J. Cancer, 2001, 94: 579-585), Id proteins (Benezra, R. Trends Cardiovasc. Med., 2001, 11(6):237-41), proteases such as uPA, uPAR, and matrix metalloproteinases (MMP-2, MMP-9; Djonov, et al. J. Pathol., 2001, 195(2):147-55), nitric oxide synthase (Am. J. Ophthalmol., 2001, 132(4):551-6), aminopeptidase (Rouslhati, E. Nature Cancer, 2: 84-90, 2002), thrombospondins (i.e., TSP-1, TSP-2; Alvarez, et al. Gynecol. Oncol., 2001, 82(2):273-8; Seki, et al. Int. J. Oncol., 2001, 19(2):305-10), k-ras (Zhang, et al. Cancer Res., 2001, 61(16):6050-4), Wnt (Zhang, et al. Cancer Res., 2001, 61(16):6050-4), cyclin-dependent kinases (CDKs; Drug Resist. Updat. 2000, 3(2):83-88), microtubules (Timar, et al. 2001. Path. Oncol. Res., 7(2): 85-94), heat shock proteins (i.e., HSP90 (Timar, supra)), heparin-binding factors (i.e., heparinase; Gohji, et al. Int. J. Cancer, 2001, 95(5):295-301), synthases (i.e., ATP synthase, thymidilate synthase), collagen receptors, integrins (i.e., αvβ3, αvβ5, α1β1, α2β1, α5β1), the surface proteolglycan NG2, AAC2-1 (SEQ ID NO.:1), or AAC2-2 (SEQ ID NO.:2), among others, including "wild-type" (i.e., normally encoded by the genome, naturally-occurring), modified, mutated versions as well as other fragments and derivatives thereof. Any of these targets may be suitable in practicing the present invention, either alone or in combination with one another or with other agents.

In certain embodiments, a nucleic acid molecule encoding an immunogenic target is utilized. The nucleic acid molecule may comprise or consist of a nucleotide sequence encoding one or more immunogenic targets, or fragments or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

An isolated nucleic acid molecule is one that: (1) is separated from at least about 50 percent of proteins, lipids, carbohydrates, or other materials with which it is naturally found when total nucleic acid is isolated from the source cells; (2) is not be linked to all or a portion of a polynucleotide to which the nucleic acid molecule is linked in nature; (3) is operably linked to a polynucleotide which it is not linked to in nature; and/or, (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. As used herein, the term "naturally occurring" or "native" or "naturally found" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The identity of two or more nucleic acid or polypeptide molecules is determined by comparing the sequences. As known in the art, "identity" means the degree of sequence relatedness between nucleic acid molecules or polypeptides as determined by the match between the units making up the molecules (i.e., nucleotides or amino acid residues). Identity measures the percent of identical matches between the smaller of two or more sequences with gap alignments (if any) addressed by a particular mathematical model or computer program (i.e., an algorithm). Identity between nucleic acid sequences may also be determined by the ability of the related sequence to hybridize to the nucleic acid sequence or isolated nucleic acid molecule. In defining such sequences, the term "highly stringent conditions" and "moderately stringent conditions" refer to procedures that permit hybridization of nucleic acid strands whose sequences are complementary, and to exclude hybridization of significantly mismatched nucleic acids. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. (see, for example, Sambrook, Fritsch & Maniatis, *Molecular Cloning: A Laboratory Manual* (2nd ed., Cold Spring Harbor Laboratory, 1989); Anderson el al., *Nucleic Acid Hybridisation: A Practical Approach* Ch. 4 (IRL Press Limited)). The term "moderately stringent conditions" refers to conditions under which a DNA duplex with a greater degree of base pair mismatching than could occur under "highly stringent conditions" is able to form. Exemplary moderately stringent conditions are 0.015 M sodium chloride, 0.0015 M sodium citrate at 50-65° C. or 0.015 M sodium chloride, 0.0015 M sodium citrate, and 20% formamide at 37-50° C. By way of example, moderately stringent conditions of 50° C. in 0.015 M sodium ion will allow about a 21% mismatch. During hybridization, other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH.

In preferred embodiments of the present invention, vectors are used to transfer a nucleic acid sequence encoding a polypeptide to a cell. A vector is any molecule used to transfer a nucleic acid sequence to a host cell. In certain cases, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is preferably capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence may be located upstream or downstream from the coding sequence and affect transcription of the sequence.

In certain embodiments, it is preferred that the flanking sequence is a trascriptional regulatory region that drives high-level gene expression in the target cell. The transcriptional regulatory region may comprise, for example, a promoter, enhancer, silencer, repressor element, or combinations thereof. The transcriptional regulatory region may be either constitutive, tissue-specific, cell-type specific (i.e., the region is drives higher levels of transcription in a one type of tissue or cell as compared to another), or regulatable (i.e., responsive to interaction with a compound such as tetracycline). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions may be utilized in practicing the present invention.

Suitable transcriptional regulatory regions include the CMV promoter (i.e., the CMV-immediate early promoter); promoters from eukaryotic genes (i.e., the estrogen-inducible chicken ovalbumin gene, the interferon genes, the glucocorticoid-inducible tyrosine aminotransferase gene, and the thymidine kinase gene); and the major early and late adenovirus gene promoters; the SV40 early promoter region (Bernoist and Chambon, 1981, *Nature* 290:304-10): the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner el al., 1981, *Proc. Natl. Acad. Sci.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.,* 75:3727-31); or the tac promoter (DeBoer et al., 1983, *Proc. Natl. Acad. Sci. U.S.A.,* 80:21-25). Tissue- and/or cell-type specific transcriptional control regions include, for example, the elastase 1 gene control region which is active in pancreatic acinar cells (Swift et al., 1984, *Cell* 38:639-46; Ornitz el al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.,* 7:1436-44); the mouse mammary tumor virus control region in testicular, breast, lymphoid and mast cells (Leder et al., 1986, *Cell* 45:485-95); the albtimin gene control region in liver (Pinkert el al., 1987, *Genes and Devel.* 1:268-76); the alpha-feto-protein gene control region in liver (Krumlauf et al., 1985, *Mol. Cell. Biol.,* 5:1639-48; Hammer et al., 1987, *Science* 235:53-58); the alpha 1-antitrypsin gene control region in liver (Kelsey et al., 1987, *Genes and Devel.* 1:161-71); the beta-globin gene control region in myeloid cells (Mogram et al., 1985, *Nature* 315:338-40; Kollias et al., 1986, *Cell* 46:89-94); the myelin basic protein gene control region in oligodendrocyte cells in the brain (Readhead et al., 1987, *Cell* 48:703-12); the myosin light chain-2 gene control region in skeletal muscle (Sani, 1985, *Nature* 314:283-86); the gonadotropic releasing hormone gene control region in the hypothalamus (Mason et al., 1986, *Science* 234:1372-78), and the tyrosinase promoter in melanoma cells (Hart, I. Semin Oncol 1996 Feb.; 23(1):154-8; Siders, et al. Cancer Gene Ther 1998 Sep.-Oct.; 5(5):281-91), among others. Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

While preparing reagents of the present invention, cells may need to be transfected or transformed. Transfection refers to the uptake of foreign or exogenous DNA by a cell, and a cell has been transfected when the exogenous DNA has been introduced inside the cell membrane. A number of transfection techniques are well known in the art (i.e., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197). Such techniques can be used to introduce one or more exogenous DNA moieties into suitable host cells.

In certain embodiments, it is preferred that transfection of a cell results in transformation of that cell. A cell is transformed when there is a change in a characteristic of the cell, being transformed when it has been modified to contain a new nucleic acid. Following transfection, the transfected nucleic acid may recombine with that of the cell by physically integrating into a chromosome of the cell, may be maintained transiently as an episomal element without being replicated, or may replicate independently as a plasmid. A cell is stably transformed when the nucleic acid is replicated with the division of the cell.

The present invention further provides isolated immunogenic targets in polypeptide form. A polypeptide is considered isolated where it: (1) has been separated from at least about 50 percent of polynucleotides, lipids, carbohydrates, or other materials with which it is naturally found when isolated from the source cell; (2) is not linked (by covalent or noncovalent interaction) to all or a portion of a polypeptide to which the "isolated polypeptide" is linked in nature; (3) is operably linked (by covalent or noncovalent interaction) to a polypeptide with which it is not linked in nature; or, (4) does not occur in nature. Preferably, the isolated polypeptide is substantially free from any other contaminating polypeptides or other contaminants that are found in its natural environment that would interfere with its therapeutic, diagnostic, prophylactic or research use.

Immunogenic target polypeptides may be mature polypeptides, as defined herein, and may or may not have an amino terminal methionine residue, depending on the method by which they are prepared. Further contemplated are related polypeptides such as, for example, fragments, variants (i.e., allelic, splice), orthologs, homologues, and derivatives, for example, that possess at least one characteristic or activity (i.e., activity, antigenicity) of the immunogenic target. Also related are peptides, which refers to a series of contiguous amino acid residues having a sequence corresponding to at least a portion of the polypeptide from which its sequence is derived. In preferred embodiments, the peptide comprises about 5-10 amino acids, 10-15 amino acids, 15-20 amino acids, 20-30 amino acids, or 30-50 amino acids. In a more preferred embodiment, a peptide comprises 9-12 amino acids, suitable for presentation upon Class I MHC molecules, for example.

A fragment of a nucleic acid or polypeptide comprises a truncation of the sequence (i.e., nucleic acid or polypeptide) at the amino terminus (with or without a leader sequence) and/or the carboxy terminus. Fragments may also include variants (i.e., allelic, splice), orthologs, homologues, and other variants having one or more amino acid additions or substitutions or internal deletions as compared to the parental sequence. In preferred embodiments, truncations and/or deletions comprise about 10 amino acids, 20 amino acids, 30 amino acids, 40 amino acids, 50 amino acids, or more. The polypeptide fragments so produced will comprise about 10 amino acids, 25 amino acids, 30 amino acids, 40 amino acids, 50 amino acids, 60 amino acids, 70 amino acids, or more. Such polypeptide fragments may optionally comprise an amino terminal methionine residue. It will be appreciated that such fragments can be used, for example, to generate antibodies or cellular immune responses to immunogenic target polypeptides.

A variant is a sequence having one or more sequence substitutions, deletions, and/or additions as compared to the subject sequence. Variants may be naturally occurring or artificially constructed. Such variants may be prepared from the corresponding nucleic acid molecules. In preferred embodiments, the variants have from 1 to 3, or from 1 to 5, or from 1 to 10, or from 1 to 15, or from 1 to 20, or from 1 to 25, or from 1 to 30, or from 1 to 40, to 50, or more than 50 amino acid substitutions, insertions, additions and/or deletions.

An allelic variant is one of several possible naturally-occurring alternate forms of a gene occupying a given locus on a chromosome of an organism or a population of organisms. A splice variant is a polypeptide generated from one of several RNA transcript resulting from splicing of a primary transcript. An ortholog is a similar nucleic acid or polypeptide sequence from another species. For example, the mouse and human versions of an immunogenic target polypeptide may be considered orthologs of each other. A derivative of a sequence is one that is derived from a parental sequence those sequences having substitutions, additions, deletions, or chemically modified variants. Variants may also include fusion proteins, which refers to the fusion of one or more first sequences (such as a peptide) at the amino or carboxy terminus of at least one other sequence (such as a heterologous peptide).

"Similarity" is a concept related to identity, except that similarity refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Substitutions may be conservative, or non-conservative, or any combination thereof. Conservative amino acid modifications to the sequence of a polypeptide (and the corresponding modifications to the encoding nucleotides) may produce polypeptides having functional and chemical characteristics similar to those of a parental polypeptide. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table 1.

TABLE I

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptide using well-known techniques. For identifying suitable areas of the molecule that may be changed without destroying biological activity (i.e., MHC binding, immunogenicity), one skilled in the art may target areas not believed to be important for that activity. For example, when similar polypeptides with similar activities from the same species or from other species are known, one skilled in the art may compare the amino acid sequence of a polypeptide to such similar polypeptides. By performing such analyses, one can identify residues and portions of the molecules that are conserved among similar polypeptides. It will be appreciated that changes in areas of the molecule that are not conserved relative to such similar polypeptides would be less likely to adversely affect the biological activity and/or structure of a polypeptide. Similarly, the residues required for binding to MHC are known, and may be modified to improve binding. However, modifications resulting in decreased binding to MHC will not be appropriate in most situations. One skilled in the art would also know that, even in relatively conserved regions, one may substitute chemically similar amino acids for the naturally occurring residues while retaining activity. Therefore, even areas that may be important for biological activity or for structure may be subject to conservative amino acid substitutions without destroying the biological activity or without adversely affecting the polypeptide structure.

Other preferred polypeptide variants include glycosylation variants wherein the number and/or type of glycosylation sites have been altered compared to the subject amino acid sequence. In one embodiment, polypeptide variants comprise a greater or a lesser number of N-linked glycosylation sites than the subject amino acid sequence. An N-linked glycosylation site is characterized by the sequence Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. To affect O-linked glycosylation of a polypeptide, one would modify serine and/or threonine residues.

Additional preferred variants include cysteine variants, wherein one or more cysteine residues are deleted or substituted with another amino acid (e.g., serine) as compared to the subject amino acid sequence set. Cysteine variants are useful when polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, the isolated polypeptides of the current invention include fusion polypeptide segments that assist in purification of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein. Suitable fusion segments include, among others, metal binding domains (e.g., a poly-histidine segment), immunoglobulin binding domains (i.e., Protein A, Protein G, T cell, B cell, Fc receptor, or complement protein antibody-binding domains), sugar binding domains (e.g., a maltose binding domain), and/or a "tag" domain (i.e., at least a portion of α-galactosidase, a strep tag peptide, a T7 tag peptide, a FLAG peptide, or other domains that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage. As described below, fusions may also be made between a TA and a co-stimulatory components such as the chemokines CXC10 (IP-10), CCL7 (MCP-3), or CCL5 (RANTES), for example.

A fusion motif may enhance transport of an immunogenic target to an MHC processing compartment, such as the endoplasmic reticulum. These sequences, referred to as tranduction or transcytosis sequences, include sequences derived from HIV tat (see Kim et al. 1997 J. Immunol. 159:1666), *Drosophila* antennapedia (see Schutze-Redelmeier et al. 1996 J. Immunol. 157:650), or human period-1 protein (hPER1; in particular. SRRHHCRSKAKRSRHH).

In addition, the polypeptide or variant thereof may be fused to a homologous polypeptide to form a homodimer or to a heterologous polypeptide to form a heterodimer. Heterologous peptides and polypeptides include, but are not limited to: an epitope to allow for the detection and/or isolation of a fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide or variant thereof.

In certain embodiments, it may be advantageous to combine a nucleic acid sequence encoding an immunogenic target, polypeptide, or derivative thereof with one or more co-stimulatory component(s) such as cell surface proteins, cytokines or chemokines in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. *Nature* 1999, 397: 263-265; Peach, et al. *J Exp Med* 1994, 180: 2049-2058) such as the CD28 binding polypeptides B7.1 (CD80; Schwartz, 1992; Chen et al, 1992; Ellis, et al. *J. Immunol.*, 156(8): 2700-9) and B7.2 (CD86; Ellis, et al. *J. Immunol.*, 156(8): 2700-9); polypeptides which bind members of the integrin family (i.e., LFA-1 (CD11a/CD18); Sedwick, et al. *J. Immunol* 1999, 162: 1367-1375; Wülfing, et al. *Science* 1998, 282: 2266-2269; Lub, et al. *Immunol Today* 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. *J. Immunol* 1997, 158: 4036-4044)) such as CD58 (LFA-3; CD2 ligand; Davis, et al. *Immunol Today* 1996, 17: 177-187) or SLAM ligands (Sayos, et al. *Nature* 1998, 395: 462-469); polypeptides which bind heat stable antigen (HSA or CD24; Zhou, et al. *Eur J Immunol* 1997, 27: 2524-2528); polypeptides which bind to members of the TNF receptor (TNFR) family (i.e., 4-1BB (CD137; Vinay, et al. *Semin Immunol* 1998, 10: 481-489), OX40 (CD134; Weinberg, et al. *Semin Immunol* 1998, 10:471-480; Higgins, et al. *J Immunol* 1999, 162: 486-493), and CD27 (Lens, et al. *Semin Immunol* 1998, 10: 491-499)) such as 4-1BBL (4-1BB ligand; Vinay, et al. *Semin, Immunol* 1998, 10: 481-48; DeBenedette, et al. *J Immunol* 1997, 158: 551-559), TNFR associated factor-1 (TRAF-1; 4-1BB ligand; Saoulli, et al. *J Exp Med* 1998, 187: 1849-1862, Arch, et al. *Mol Cell Biol* 1998, 18: 558-565), TRAF-2 (4-1 BB and OX40 ligand; Saoulli, et al. *J Exp Med* 1998, 187: 1849-1862; Oshima, et al. *Int Immunol* 1998, 10: 517-526, Kawamata, et al. *J Biol Chem* 1998, 273: 5808-5814), TRAF-3 (4-1BB and OX40 ligand; Arch, et al. *Mol Cell Biol* 1998, 18: 558-565; Jang, et al. *Biochem Biophys. Res Commun,* 1998, 242: 613-620; Kawamata S, et al. *J Biol Chem* 1998, 273: 5808-5814), OX40L (OX40 ligand; Gramaglia, et al. *J Immunol* 1998, 161: 6510-6517), TRAF-5 (OX40 ligand; Arch, et al. *Mol Cell Biol* 1998, 18: 558-565; Kawamata, et al. *J Biol Chem* 1998, 273: 5808-5814), and CD70 (CD27 ligand; Couderc, et al. *Cancer Gene Ther.,* 5(3): 163-75). CD154 (CD40 ligand or "CD40L"; Gurunathan, et al. *J. Immunol.,* 1998, 161: 4563-4571; Sine, et al. *Hum. Gene Ther.,* 2001, 12: 1091-1102) may also be suitable.

One or more cytokines may also be suitable co-stimulatory components or "adjuvants", either as polypeptides or being encoded by nucleic acids contained within the compositions of the present invention (Parmiani, et al. Immunol Lett 2000 Sep. 15; 74(1): 41-4; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 Jul.-Aug.; 2(4):243-9; Rao, et al. *J. Immunol.* 156: 3357-3365 (1996)), IL-15 (Xin, et al. *Vaccine,* 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood,* 88: 202-210 (1996)), tumor necrosis factor-alpha (TNF-α), or interferon-gamma (INF-γ). Other cytokines may also be suitable for practicing the present invention, as is known in the art.

Chemokines may also be utilized. For example, fusion proteins comprising CXCL10 (IP-10) and CCL7 (MCP-3) fused to a tumor self-antigen have been shown to induce anti-tumor immunity (Biragyn, et al. *Nature Biotech.* 1999, 17: 253-258). The chemokines CCL3 (MIP-1α) and CCL5 (RANTES) (Boyer, et al. *Vaccine,* 1999, 17 (Supp. 2): S53-S64) may also be of use in practicing the present invention. Other suitable chemokines are known in the art.

It is also known in the art that suppressive or negative regulatory immune mechanisms may be blocked, resulting in enhanced immune responses. For instance, treatment with anti-CTLA-4 (Shrikant, et al. *Immunity,* 1996, 14: 145-155; Sutmuller, et al. *J. Exp. Med.,* 2001, 194: 823-832), anti-CD25 (Sutmuller, supra), anti-CD4 (Matsui, et al. *J. Immunol.,* 1999, 163: 184-193), the fusion protein IL13Ra2-Fc (Terabe, et al. *Nature Immunol.,* 2000, 1: 515-520), and combinations thereof (i.e., anti-CTLA-4 and anti-CD25, Sutmuller, supra) have been shown to upregulate anti-tumor immune responses and would be suitable in practicing the present invention.

Any of these components may be used alone or in combination with other agents. For instance, it has been shown that a combination of CD80, ICAM-1 and LFA-3 ("TRICOM") may potentiate anti-cancer immune responses (Hodge, et al. *Cancer Res.* 59: 5800-5807 (1999). Other effective combinations include, for example, IL-12+GM-CSF (Ahlers, et al. *J. Immunol.,* 158: 3947-3958 (1997); Iwasaki, et al. *J. Immunol.* 158: 4591-4601 (1997)), IL-12+GM-CSF+TNF-α (Ahlers, et al. *Int. Immunol.* 13: 897-908 (2001)), CD80+IL-12 (Fruend, et al. *Int. J. Cancer,* 85: 508-517 (2000); Rao, et al. supra), and CD86+GM-CSF+IL-12 (Iwasaki, supra). One of skill in the art would be aware of additional combinations useful in carrying out the present invention. In addition, the skilled artisan would be aware of additional reagents or methods that may be used to modulate such mechanisms. These reagents and methods, as well as others known by those of skill in the art, may be utilized in practicing the present invention.

Additional strategies for improving the efficiency of nucleic acid-based immunization may also be used including, for example, the use of self-replicating viral replicons (Caley, et al. 1999. *Vaccine,* 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J. Virol.* 75: 4947-4951), in viva electroporation (Widera, et al. 2000. *J. Immunol.* 164: 4635-3640), incorporation of CpG stimulatory motifs (Gurunathan, et al. *Ann. Rev. Immunol.,* 2000, 18: 927-974; Leitner, supra), sequences for targeting of the endocytic or ubiquitin-processing pathways (Thomson, et al. 1998. *J. Virol.* 72: 2246-2252; Velders, et al. 2001. *J. Immunol.* 166: 5366-5373), prime-boost regimens (Gurunathan, supra; Sullivan, et al. 2000. *Nature,* 408: 605-609; Hanke, et al. 1998. *Vaccine,* 16: 439-445; Amara, et al. 2001. *Science,* 292: 69-74), and the use of mucosal delivery vectors such as *Salmonella* (Darji, et al. 1997. *Cell,* 91: 765-775; Woo, et al. 2001. *Vaccine,* 19: 2945-2954). Other methods are known in the art, some of which are described below.

Chemotherapeutic agents, radiation, anti-angiogenic compounds, or other agents may also be utilized in treating and/or preventing cancer using immunogenic targets (Sebti, et al. *Oncogene* 2000 Dec. 27; 19(56):6566-73). For example, in treating Metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+methotrexate+5-fluorouracil; cyclophosphamide+doxorubicin+5-fluorouracil; or, cyclophosphamide+doxorubicin, for example. Other compounds such as prednisone, a taxane, navelbine, mitomycin C, or vinblastine have been utlized for various reasons. A majority of breast cancer patients have estrogen-receptor positive (ER+) tumors and in these patients, endocrine therapy (i.e., tamoxifen) is preferred over chemotherapy. For such patients, tamoxifen or, as a second line therapy, progestins (medroxyprogesterone acetate or megestrol acetate) are preferred. Aromatase inhibitors (i.e., aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED 1522 (Merck KgaA) may also be suitable for use. As such, immunological targeting of immunogenic targets associated with colorectal cancer could be performed in combination with a treatment using those chemotherapeutic agents. Similarly, chemotherapeutic agents used to treat other types of cancers are well-known in the art and may be combined with the immunogenic targets described herein.

Many anti-angiogenic agents are known in the art and would be suitable for co-administration with the immunogenic target vaccines (see, for example, Timar, et al. 2001. *Pathology Oncol. Res.,* 7(2): 85-94). Such agents include, for example, physiological agents such as growth factors (i.e., ANG-2, NK1,2,4 (HGF), transforming growth factor beta (TGF-β)); cytokines (i.e., interferons such as IFN-α, -β, -γ, platelet factor 4 (PF-4), PR-39), proteases (i.e., cleaved AT-III, collagen XVIII fragment (Endostatin)), HinwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PAI-1; pigment epithelium derived factor (PEDF)), Tumstatin (available through ILEX, Inc.), antibody products (i.e., the collagen-binding antibodies HUIV26, HUI77, XL313; anti-VEGF; anti-integrin (i.e., Vitaxin, (Lxsys))), and glycosidases (i.e., heparinase-I, -III). "Chemical" or modified physiological agents known or believed to have anti-angiogenic potential include, for example, vinblastine, taxol, ketoconazole, thalidomide, dolestatin, combrestatin A, rapamycin (Guba, et al. 2002, *Nature Med.,* 8: 128-135), CEP-7055 (available from Cephalon, Inc.), flavone acetic acid, Bay 12-9566 (Bayer Corp.), AG3340 (Agouron, Inc.), CGS 27023A (Novartis), tetracylcine derivatives (i.e., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974

(Merck KcgaA), tyrphostins, isoquinolones, retinoic acid, carboxyamidotriazole, TNP-470, octreotide, 2-methoxyestradiol, aminosterols (i.e., squalamine), glutathione analogues (i.e., N-acteyl-L-cysteine), combretastatin A-4 (Oxigene), Eph receptor blocking agents (*Nature,* 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phanylalanin-N-methylamides (i.e., Batimistat, Marimastat), AG3340, and minocycline. Many other suitable agents are known in the art and would suffice in practicing the present invention.

The present invention may also be utilized in combination with "non-traditional" methods of treating cancer. For example, it has recently been demonstrated that administration of certain anaerobic bacteria may assist in slowing tumor growth. In one study, *Clostridium novyi* was modified to eliminate a toxin gene carried on a phage episome and administered to mice with colorectal tumors (Dang, et al. *P.N.A.S. USA,* 98(26): 15155-15160, 2001). In combination with chemotherapy, the treatment was shown to cause tumor necrosis in the animals. The reagents and methodologies described in this application may be combined with such treatment methodologies.

Nucleic acids encoding immunogenic targets may be administered to patients by any of several available techniques. Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include ψ2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, *Hum. Gene Ther.,* 5 (3): 343-79; Culver, K., et al., *Cold Spring Harb. Symp. Quant. Biol.,* 59: 685-90); Oldfield, E., 1993, *Hum. Gene Ther.,* 4(1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, *Science,* 252 (5004): 431-4; Crystal, R., et al., 1994, *Nat. Genet.,* 8 (1): 42-51), the study eukaryotic gene expression (Levrero, M., et al., 1991, *Gene,* 101 (2): 195-202), vaccine development (Graham, F. and Prevec, L., 1992, *Biotechnology,* 20: 363-90), and in animal models (Stratford-Perricaudet, L., et al., 1992, *Bone Marrow Transplant.,* 9 (Suppl. 1): 151-2; Rich, D., et al., 1993, *Hum. Gene Ther.,* 4 (4): 461-76). Experimental routes for administrating recombinant Ad to different tissues in vivo have included intratracheal instillation (Rosenfeld, M., et al, 1992, *Cell,* 68 (1): 143-55) injection into muscle (Quantin, B., et al., 1992, *Proc. Natl. Acad. Sci. U.S.A.,* 89 (7): 2581-4), peripheral intravenous injection (Herz, J., and Gerard, R., 1993, *Proc. Natl. Acad. Sci. U.S.A.,* 90 (7): 2812-6) and stereotactic inoculation to brain (Le Gal La Salle, G., et al., 1993, *Science,* 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.,* 81 (20): 6466-70). And Herpes Simplex Virus type-1 (HSV-1) is yet another attractive vector system, especially for use in the nervous system because of its neurotropic property (Geller, A., et al., 1991, *Trends Neurosci.,* 14 (10): 428-32; Glorioso, el al., 1995, *Mol. Biotechnol.,* 4 (1): 87-99; Glorioso, et al., 1995, *Annu. Rev. Microbiol.,* 49: 675-710).

Poxvirus is another useful expression vector (Smith, et al. 1983, *Gene,* 25 (1): 21-8; Moss, et al, 1992, *Biotechnology,* 20: 345-62; Moss, et al, 1992, *Curr. Top. Microbiol. Immunol.,* 158: 25-38; Moss, et al. 1991. *Science,* 252: 1662-1667). Poxviruses shown to be useful include vaccinia, NYVAC, avipox, fowlpox, canarypox, ALVAC, and ALVAC(2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R); hemorrhagic region (u; B13R+B14R); A type inclusion body region (ATI; A26L); hemagglutinin gene (HA; A56R); host range gene region (C7L-K1L); and, large subunit, ribonucleotide reductase (14L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265, 189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use in practicing the present invention (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a,b; U.S. Pat. No. 5,833, 975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in practicing the present invention. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLEI-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, Calif.). Bacterial vectors may also be used with the current invention. These vectors include, for example, *Shigella, Salmonella, Vibrio cholerae, Lactobacillus, Bacille guérin (BCG), and Streptococcus* (see for example, WO 88/6626; WO 90/0594; WO 91/13157; WO 92/1796; and WO 92/21376). Many other non-viral plasmid expression vectors and systems are known in the art and could be used with the current invention.

Suitable nucleic acid delivery techniques include DNA-ligand complexes, adenovirus-Inland-DNA complexes, direct injection of DNA, $CaPO_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.*, 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

An immunogenic target may also be administered in combination with one or more adjuvants to boost the immune response. Exemplary adjuvants are shown in Table I below:

TABLE I

Types of Immunologic Adjuvants

| Type of Adjuvant | General Examples | Specific Examples/References |
|---|---|---|
| 1 Gel-type | Aluminum hydroxide/phosphate ("alum adjuvants") | (Aggerbeck and Heron, 1995) |
|  | Calcium phosphate | (Relyveld, 1986) |
| 2 Microbial | Muramyl dipeptide (MDP) | (Chedid et al., 1986) |
|  | Bacterial exotoxins | Cholera toxin (CT), *E. coli* labile toxin (LT)(Freytag and Clements, 1999) |
|  | Endotoxin-based adjuvants | Monophosphoryl lipid A (MPL) (Ulrich and Myers, 1995) |
|  | Other bacterial | CpG oligonucleotides (Corral and Petray, 2000), BCG sequences (Krieg, et al. Nature, 374: 576). tetanus toxoid (Rice, et al. J. Immunol., 2001, 167: 1558-1565) |
| 3 Particulate | Biodegradable polymer microspheres | (Gupta et al., 1998) |
|  | Immunostimulatory complexes (ISCOMs) | (Morein and Bengtsson, 1999) |
|  | Liposomes | (Wassef et al., 1994) |
| 4 Oil-emulsion and surfactant-based adjuvants | Freund's incomplete adjuvant | (Jensen et al., 1998) |
|  | Microfluidized emulsions | MF59 (Ott et al., 1995) SAF (Allison and Byars, 1992) (Allison, 1999) |
|  | Saponins | QS-21 (Kensil, 1996) |
| 5 Synthetic | Muramyl peptide derivatives | Murabutide (Lederer, 1986) Threony-MDP (Allison, 1997) |
|  | Nonionic block copolymers | L121 (Allison, 1999) |
|  | Polyphosphazene (PCPP) | (Payne et al., 1995) |
|  | Synthetic polynucleotides | Poly A: U, Poly I: C (Johnson, 1994) |

The immunogenic targets of the present invention may also be used to generate antibodies for use in screening assays or for immunotherapy. Other uses would be apparent to one of skill in the art. The term "antibody" includes antibody fragments, as are known in the art, including Fab, $Fab_2$, single chain antibodies (Fv for example), humanized antibodies, chimeric antibodies, human antibodies, produced by several methods as are known in the art. Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No.* 1, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). The antibodies or derivatives therefrom may also be conjugated to therapeutic moieties such as cytotoxic drugs or toxins, or active fragments thereof such as diptheria A chain, exotoxin A chain, ricin A chain, abrin A chain, curcin, crotin, phenomycin, enomycin, among others. Cytotoxic agents may also include radiochemicals. Antibodies and their derivatives may be incorporated into compositions of the invention for use in vitro or in vivo.

Nucleic acids, proteins, or derivatives thereof representing an immunogenic target may be used in assays to determine the presence of a disease state in a patient, to predict prognosis, or to determine the effectiveness of a chemotherapeutic or other treatment regimen. Expression profiles, performed as is known in the art, may be used to determine the relative level of expression of the immunogenic target. The level of expression may then be correlated with base levels to determine whether a particular disease is present within the patient, the patient's prognosis, or whether a particular treatment regimen is effective. For example, if the patient is being treated with a particular chemotherapeutic regimen, an decreased level of expression of an immunogenic target in the patient's tissues (i.e., in peripheral blood) may indicate the regimen is In decreasing the cancer load in that host. Similarly, if the level of expression is increasing, another therapeutic modality may need to be utilized. In one embodiment, nucleic acid probes corresponding to a nucleic acid encoding an immunogenic target may be attached to a biochip, as is known in the art, for the detection and quantification of expression in the host.

It is also possible to use nucleic acids, proteins, derivatives therefrom, or antibodies thereto as reagents in drug screening assays. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

Administration of a composition of the present invention to a host may be accomplished using any of a variety of techniques known to those of skill in the art. The composition(s) may be processed in accordance with conventional methods of pharmacy to produce medicinal agents for administration to patients, including humans and other mammals (i.e., a "pharmaceutical composition"). The pharmaceutical composition is preferably made in the form of a dosage unit containing a given amount of DNA, viral vector particles, polypeptide or peptide, for example. A suitable daily dose for a human or other mammal may vary widely depending on the condition of the patient and other factors, but, once again, can be determined using routine methods.

The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid; polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a nucleic acid or polypeptide used to induce or enhance an effective immune response. It is preferred that compositions of the present invention provide for the induction or enhancement of an anti-tumor immune response in a host which protects the host from the development of a tumor and/or allows the host to eliminate an existing tumor from the body.

For oral administration, the pharmaceutical composition may be of any of several forms including, for example, a capsule, a tablet, a suspension, or liquid, among others. Liquids may be administered by injection as a composition with suitable carriers including saline, dextrose, or water. The term parenteral as used herein includes subcutaneous, intravenous, intramuscular, intrasternal, infusion, or intraperitoneal administration. Suppositories for rectal administration of the drug can be prepared by mixing the drug with a suitable non-irritating excipient such as cocoa butter and polyethylene glycols that are solid at ordinary temperatures but liquid at the rectal temperature.

The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. For example, a poxviral vector may be administered as a composition comprising $1 \times 10^6$ infectious particles per dose. Thus, the dosage regimen may vary widely, but can be determined routinely using standard methods.

A prime-boost regimen may also be utilized (WO 01/30382 A1) in which the targeted immunogen is initially administered in a priming step in one form followed by a boosting step in which the targeted immunogen is administered in another form. The form of the targeted immunogen in the priming and boosting steps are different. For instance, if the priming step utilized a nucleic acid, the boost may be administered as a peptide. Similarly, where a priming step utilized one type of recombinant virus (i.e., ALVAC), the boost step may utilize another type of virus (i.e., NYVAC). This prime-boost method of administration has been shown to induce strong immunological responses.

While the compositions of the invention can be administered as the sole active pharmaceutical agent, they can also be used in combination with one or more other compositions or agents (i.e., other immunogenic targets, co-stimulatory molecules, adjuvants). When administered as a combination, the individual components can be formulated as separate compositions administered at the same time or different times, or the components can be combined as a single composition.

Injectable preparations, such as sterile injectable aqueous or oleaginous suspensions, may be formulated according to known methods using suitable dispersing or wetting agents and suspending agents. The injectable preparation may also be a sterile injectable solution or suspension in a non-toxic parenterally acceptable diluent or solvent. Suitable vehicles and solvents that may be employed are water, Ringer's solution, and isotonic sodium chloride solution, among others. For instance, a viral vector such as a poxvirus may be prepared in 0.4% NaCl. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

For topical administration, a suitable topical dose of a composition may be administered one to four, and preferably two or three times daily. The dose may also be administered with intervening days during which no does is applied. Suitable compositions may comprise from 0.001% to 10% w/w, for example, from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may also be prepared in a solid form (including granules, powders or suppositories). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

Pharmaceutical compositions comprising a nucleic acid or polypeptide of the present invention may take any of several forms and may be administered by any of several routes. In preferred embodiments, the compositions are administered via a parenteral route (intradermal, intramuscular or subcutaneous) to induce an immune response in the host. Alternatively, the composition may be administered directly into a lymph node (intranodal) or tumor mass (i.e., intratumoral administration). For example, the dose could be administered subcutaneously at days 0, 7, and 14. Suitable methods for immunization using compositions comprising TAs are known in the art, as shown for p53 (Hollstein et al., 1991), p21-ras (Almoguera et al., 1988), HER-2 (Fendly et al., 1990), the melanoma-associated antigens (MAGE-1; MAGE-2) (van der Bruggen et al., 1991), p97 (Hu et al., 1988), and carcinoembryonic antigen (CEA) (Kantor et al., 1993; Fishbein et al., 1992; Kaufman et al., 1991), among others.

Preferred embodiments of administratable compositions include, for example, nucleic acids or polypeptides in liquid preparations such as suspensions, syrups, or elixirs. Preferred injectable preparations include, for example, nucleic acids or polypeptides suitable for parental, subcutaneous, intradermal, intramuscular or intravenous administration such as sterile suspensions or emulsions. For example, a recombinant poxvirus may be in admixture with a suitable carrier, diluent, or excipient such as sterile water, physiological saline, glucose or the like. The composition may also be provided in lyophilized form for reconstituting, for instance, in isotonic aqueous, saline buffer. In addition, the compositions can be co-administered or sequentially administered with other antineoplastic, anti-tumor or anti-cancer agents and/or with agents which reduce or alleviate ill effects of antineoplastic, anti-tumor or anti-cancer agents.

A kit comprising a composition of the present invention is also provided. The kit can include a separate container containing a suitable carrier, diluent or excipient. The kit can also include an additional anti-cancer, anti-tumor or antineoplastic agent and/or an agent that reduces or alleviates ill effects of antineoplastic, anti-tumor or anti-cancer agents for co- or sequential-administration. Additionally, the kit can include instructions for mixing or combining ingredients and/or administration.

A better understanding of the present invention and of its many advantages will be had from the following examples, given by way of illustration.

EXAMPLES

Example 1

A. Modification of mCEA (6D) repeat 1

The presence of truncated forms of CEA in cells following expression of recombinant CEA has been documented. This study set forth to generate CEA-encoding nucleic acid sequences that do not result in the expression of truncated CEA following expression in cells. Generation and expression of a new CEA-encoding nucleic acid sequence, CAP (6D)-1,2, is described below.

The plasmid p3'H6MCEA was obtained from Virogenetics, Inc. This plasmid contains the MCEA gene with 6D modification under the control of partial H6 promoter (FIG. 1A). The 912 bp NruI-BamHI fragment from p3'H6MCEA was cloned into pUC18 to form plasmid pSE1544.9 (pUC18-mCEA repeat 1; FIG. 1B).

Figure 3:
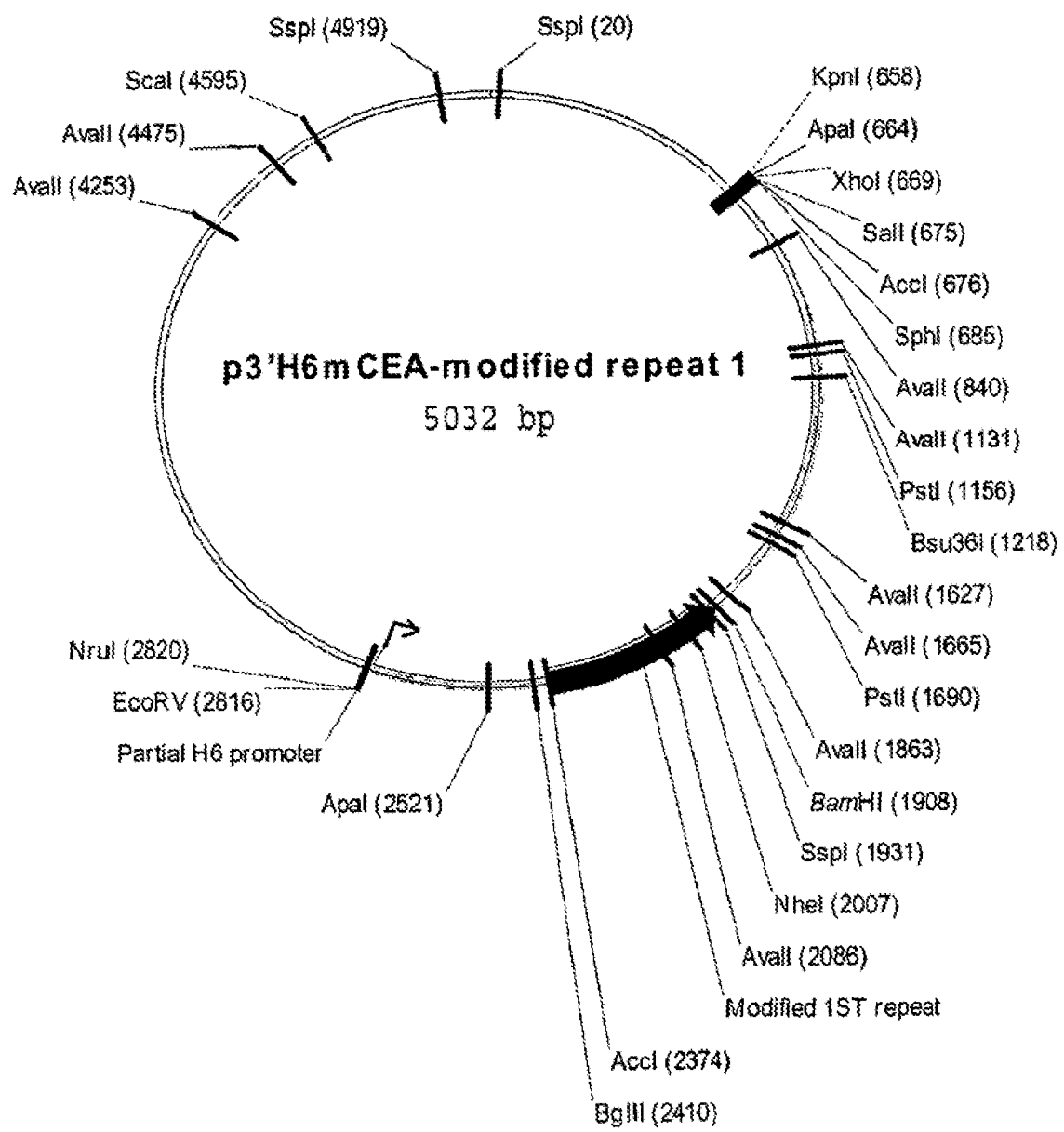
FIG. 3. Illustration of plasmid pSE1658.15 (p3'H6MCEA-modified repeat 1).

OPC purified Oligos 7524-7526, 7528-7533, 7535-7537, and 7567-7568 were kinased and annealed to create two fragments which were ligated to result in a 464 bp synthetic modified mCEA repeat 1 flanked by AccI and BamHI sites. This synthetic modified repeat 1 fragment was cloned into pSE1544.9 AccI-BamHI to create pSE1616.44 (pUC18-mCEA-modified repeat 1; FIG. 2). The 904 bp EcoRV-BamHI fragment of pSE1616.44 was cloned back into p3'H6MCEA EcoRV-BamHI to form pSE1658.15 (p3'H6MCEA-modified repeat 1; FIG. 3).

B. Modification of mCEA(6D) Repeat 2

Figure 4:
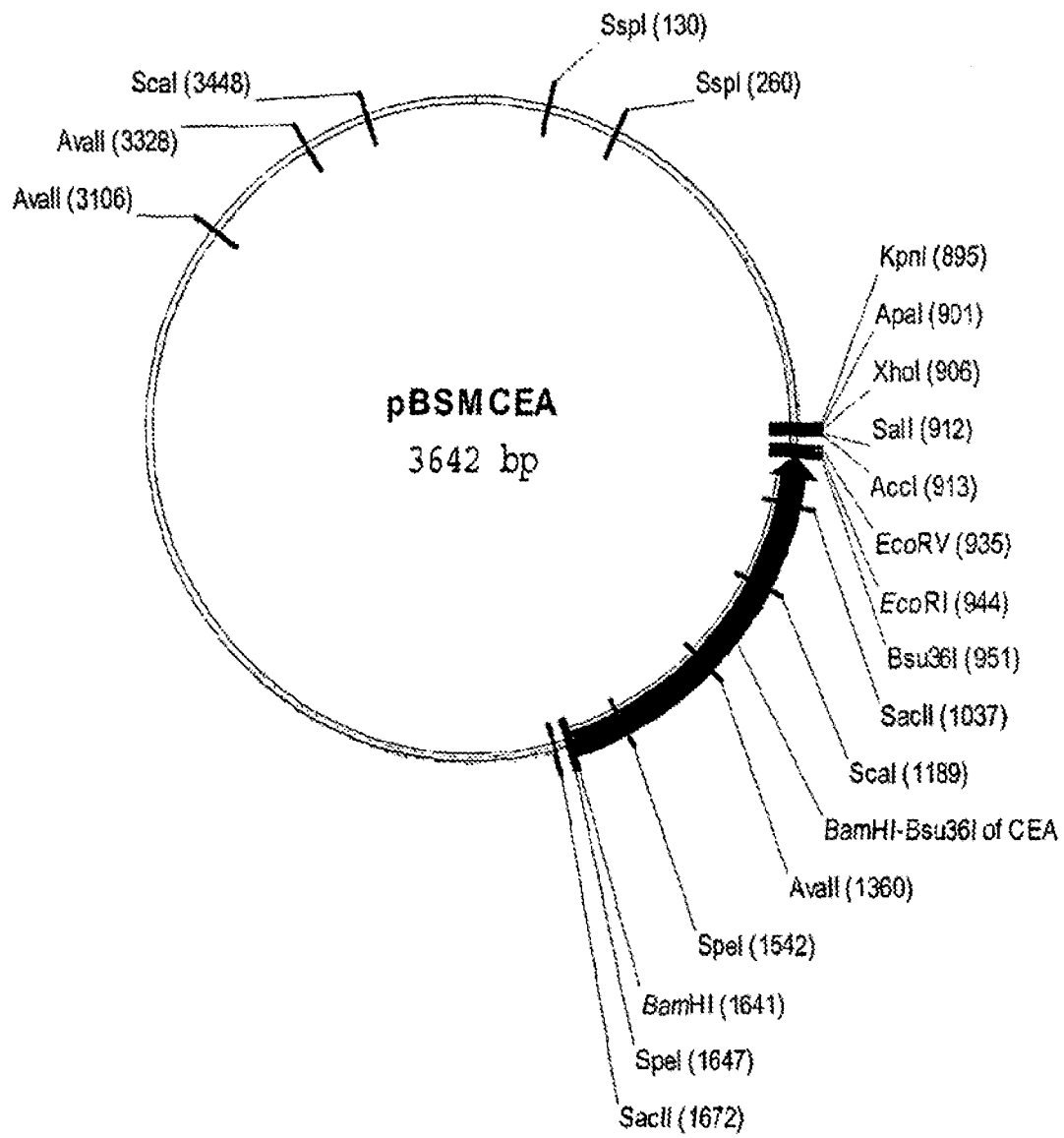
FIG. 4. Illustration of plasmid pBSmCEA.

A synthetic modified repeat 2 fragment was created by using a method called gene splicing by overlap extension (SOE) and cloned into pBluescript-SK+, generating pBSm-CEA (FIG. 4). The oligos used for the repeat 2 modification are shown below (section IV, B). The two different clones (pBS-mCEA-3 and pBS-mCEA-8) contained various point mutations.

Figure 5:
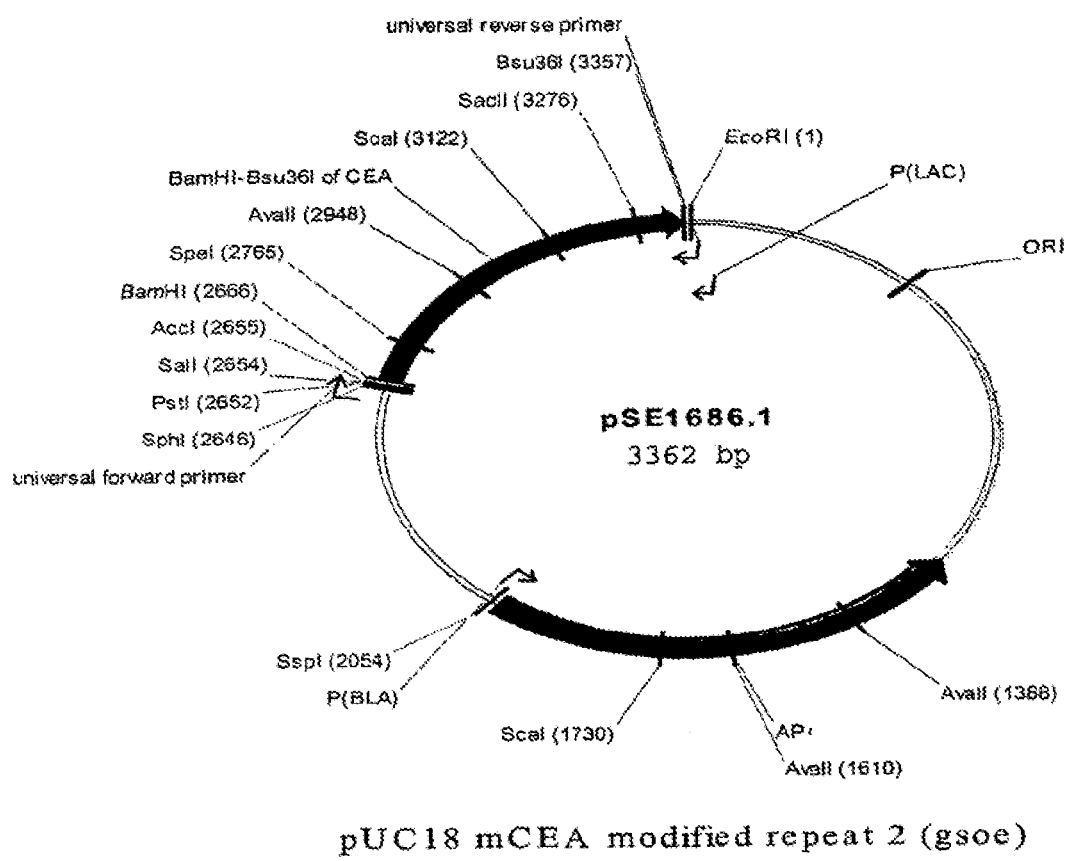
FIG. 5. Illustration of plasmid pSE1686.1 (pUC18 mCEA modified repeat 2.

The 697 bp BamHI-EcoRI fragment of pBS-mCEA-3 was cloned into pUC18 BamHI-EcoRI to create pSE1671.8. The 591 bp SpeI-Bsu361 fragment of pBS mCEA-8 was cloned into pSE1671.8 SpeI-Bsu361, generating plasmid designated pSE1681.1. Two site PCR mutagenesis, using the Quikchange site directed mutagenesis kit from Stratagene with oligos 7751 (GGACGGTAGTAGGTGTATGATG-GAGATATAGTTGGGTCGTCTGGGCC) (SEQ ID NO:24) and 7760 (CAGAATGAATTATCCGTTGATCACTCC) (SEQ ID NO:25), was performed to correct the two remaining point mutations pSE1681.1. The corrected clone was designated pSE1686.1 (pUC18 mCEA modified repeat 2; FIG. 5).

Figure 6:
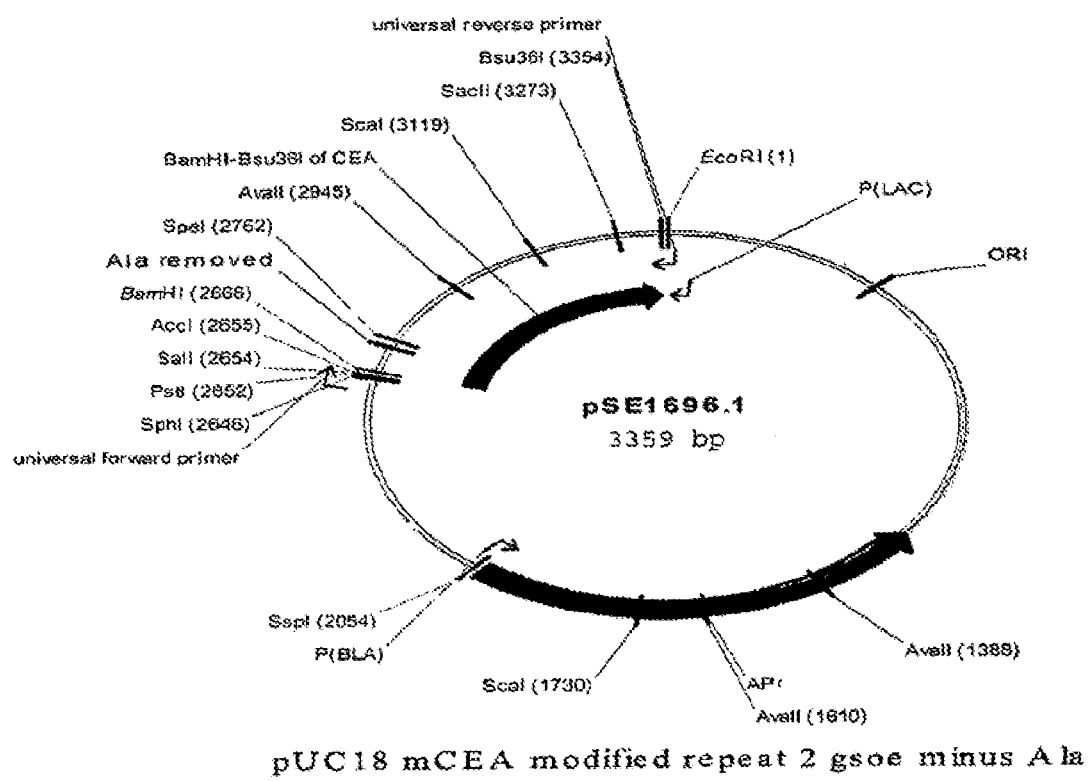
FIG. 6. Illustration of plasmid pSE1696.1 (pUC18 mCEA modified repeat 2.

As noted recently, an Alanine codon was absent from 5' terminus of the second repeat in is plasmid p3'H6MCEA which contained CEA. To preserve the consistency of the amino acid sequence of CEA, the Alanine codon present in plasmid pSE1686.1 containing the modified second repeat of CEA was knocked out. This was accomplished using oligos 7802 (CGTGACGACGATTACCGTGTATGAGC-CACCAAAACCATTCATAAC) (SEQ ID NO:26) and 7803 (GTTATGAATGGTTTTGGTGGCTCATA-CACGGTAATCGTCGTCACG) (SEQ ID NO:27) and the Quikchange site-directed mutagenesis kit from Stratagene. The resulting plasmid, pSE1696.1 (pUC18 mCEA modified repeat 2; FIG. 6) was confirmed by sequencing.

Figure 7:
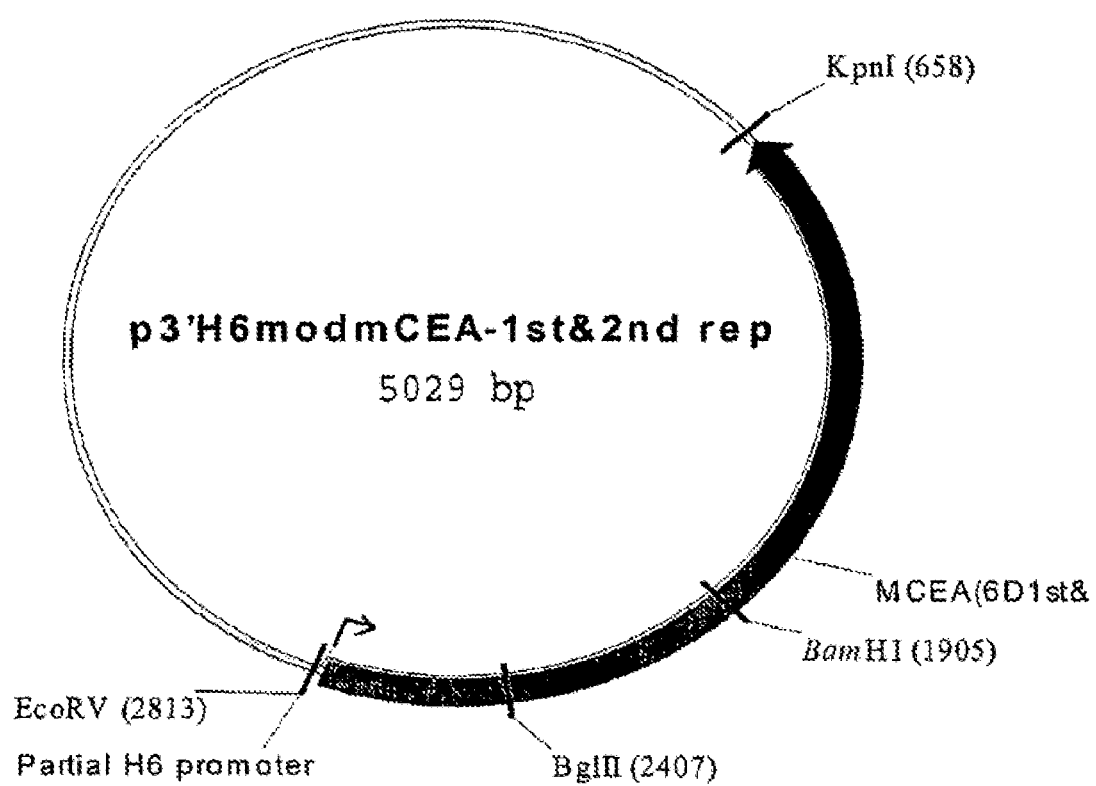
FIG. 7. Illustration of plasmid p3'H6modMCEA-1st&2nd repeats.

The 694 bp Bsu361-BamHI fragment from pSE1696.1 was cloned into Bsu361-BamHI site of Pse1658.15 to combine modified repeats 1 and 2. The generated plasmid was designated p3'H6modMCEA-1st&2nd repeats (FIG. 7).

C. Construction of ALVAC Donor Plasmid pNVQH6MCEA (6D1st&2nd)

Figure 8:
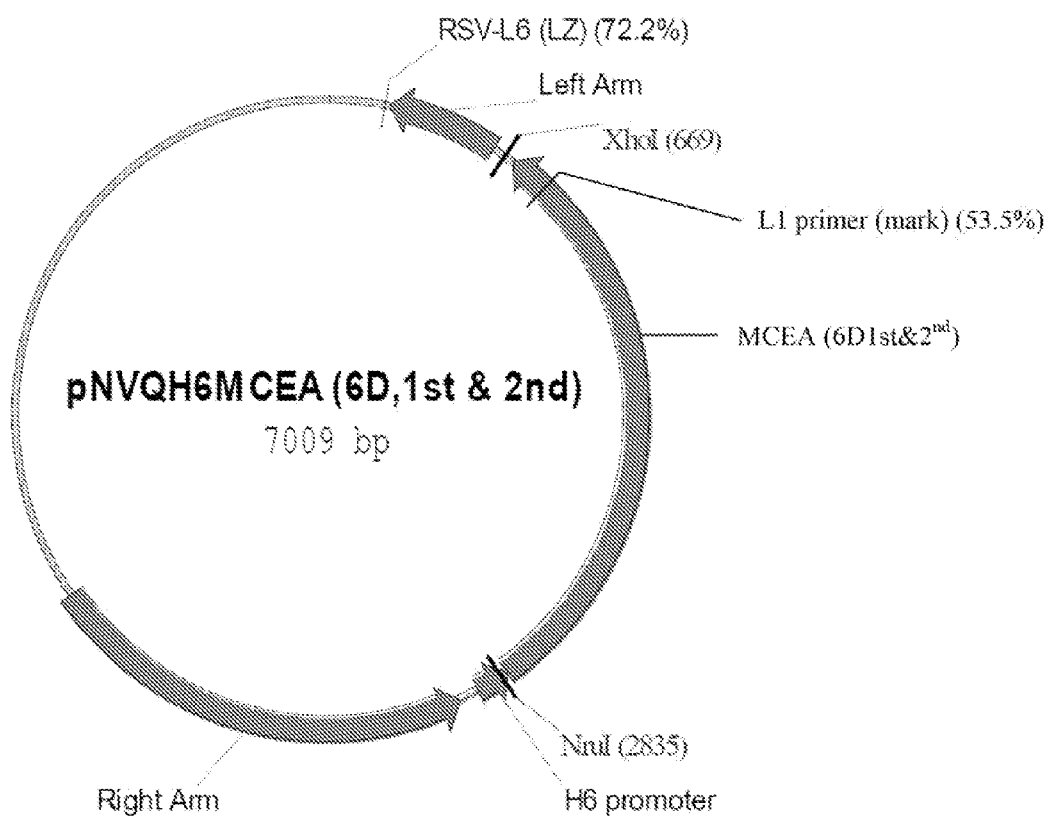
FIG. 8. Illustration of plasmid pNVQH6MCEA (6D1st&$2^{nd}$).

The 2.2 kb NruI/XhoI fragment from p3'H6modMCEA-1st&2nd repeats was cloned into NruI/XhoI site of pNVQH6LSP-18, generating pNVQH6MCEA(6D1st&2$^{nd}$; FIG. 8). The modified CEA sequence ("CAP(6D)-1,2") contained within pNVQH6MCEA is shown in FIG. 9.

D. Expression of Modified CEA

Figure 10:
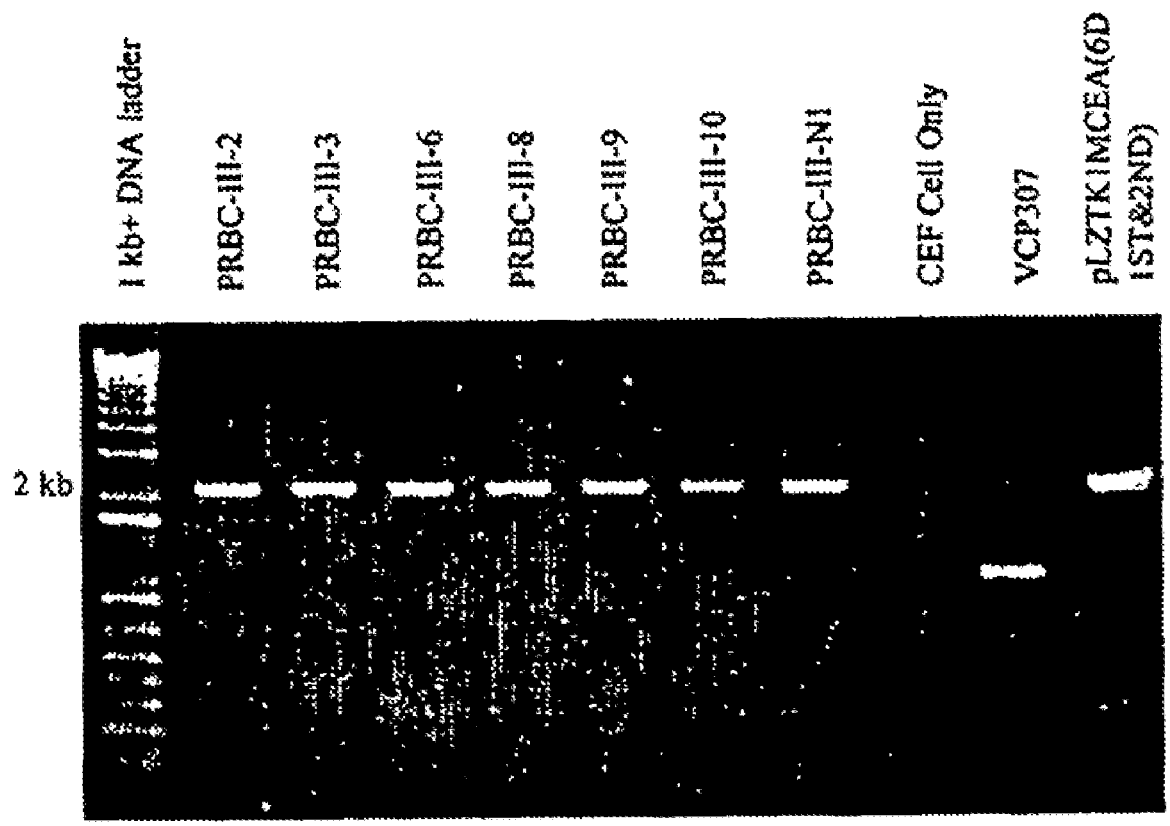
FIG. 10. PCR analysis to confirm the presence of CAP (6D)-1,2 in NYVAC DNA.

To test the stability of the CAP(6D)-1,2 sequence upon expression in a cell, the gene together with flanking H6 promoter was PCR amplified using pNVQH6MCEA (6D1ST&2ND) as template and two oligos (8034LZ: CTG-GCGCGCCTTCTTTATTCTATACTTAAAAAGTG (SEQ ID NO:29); and 8035LZ: CTGGTACCAGAAAAACTATAT-CAGAGCAACCCCAAC (SEQ ID NO:30)). The PCR product was then cloned into an NYVAC TK donor plasmid designated pLZTK1 containing the LacZ and K1L marker genes. This vector was specifically made for the generation of recombinant virus in NYVAC by using blue/white screening method. After in vitro recombination between donor plasmid pLZTK1mCCA(6D1st&2nd) and NYVAC, the foreign CAP (6D)-1,2 sequence and marker genes are integrated into the NYVAC genome. The plaques containing intermediate recombinant NYVAC with both LacZ and mCEA appeared blue. Several rounds of plaque purification were then performed. The second recombination event kicked out the marker genes resulting in the final white plaques containing recombinants with only the CAP(6D)-1,2 sequence but no marker genes (FIG. 10).

The recombinant white plaques and blue plaques were picked for confirmation of CAP(6D)-1,2 sequence expression. Infection was performed using the virus from the respective plaques and the cells were harvested three days after infection for preparing either cellular DNA or cell lysate. For isolation of recombinant NYVAC DNA, DNAzol® reagent (GibcoBRL) was used. PCR (PCR Condition: 95° C. (5 min)→[95° C.(30 sec)→49° C.(30 sec)→72° C.(1 min)]30 cycles→72° C. (7 min)→4° C.) was run to confirm the existence of CAP(6D)-1,2 sequence in the recombinant NYVAC genome. The primers used were 7569LZ (5' ttggatccatg-gagtctccctcggcc 3' (SEQ ID NO:31) forward primer) and 7570LZ (5' ttggatccctatatcagagcaacccc 3' (SEQ ID NO:32) reverse primer), which could amplify the full length 2106 bp CAP(6D)-1,2.

The final recombinant white plaques PRBC-III-2, 3, 6, 8, 9, 10 all demonstrated the 2.1 kb CAP(6D)-1,2 sequence band in PCR. PRBC-III-N1 was a blue plaque with both marker genes and CAP(6D)-1,2 sequence still in the viral genome and the CAP(6D)-1,2 sequence band was also amplified in the PCR. The prominent PCR band amplified from vCP 307 DNA (containing native CEA integrated into the ALVAC genome) was truncated CEA at 1.2 kb with a very faint full-length CEA band. The cell-only sample (no viral infection) was used as a negative control and the plasmid pLZTK1MCEA(6D1ST&2ND) was a positive control used in the PCR reaction. The PCR results clearly showed the full-length CAP(6D)-1,2 in the recombinant viral genome with no other truncated form of CEA visible. This result indicated that CAP(6D)-1,2 has increased stability relative to the native CEA in the ALVAC genome.

Figure 11:
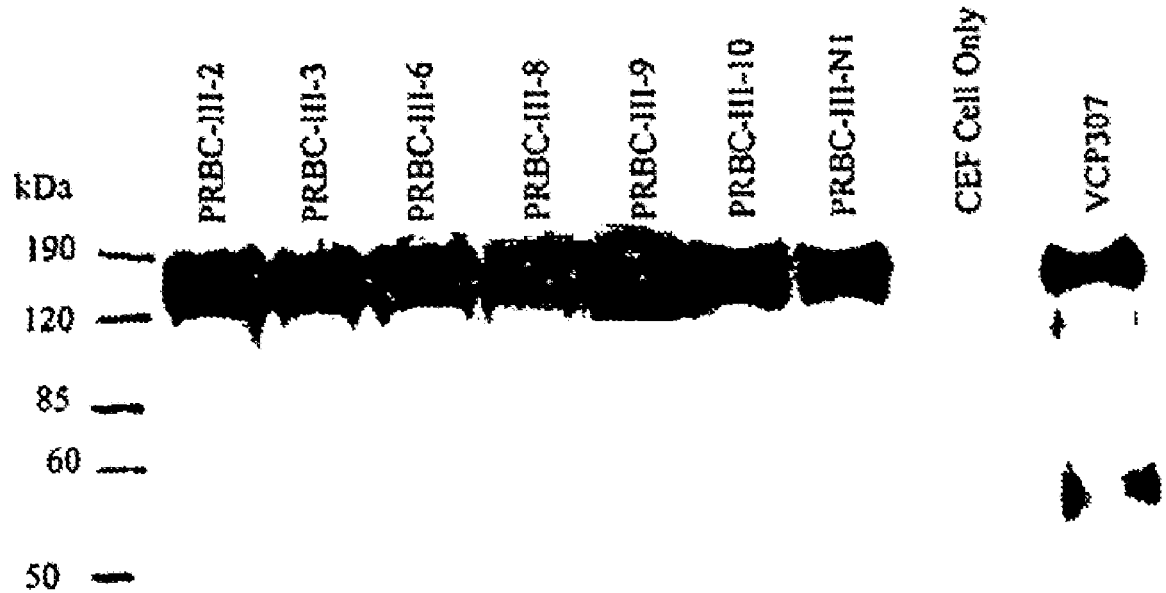
FIG. 11. Immunoblot illustrating the lack of truncated CEA in cells expressing CAP(6D)-1,2.

Protein expression was also assayed by immunoblot to confirm the absence of truncated CEA protein in cells expressing CAP(6D)-1,2 (FIG. 11). For isolation of cell lysate, cells were first washed with PBS followed by the addition of Lysis Buffer (Reporter Gene Assay; Boehringer Mannheim) and shaking for 15 minutes. Cell lysate was spun down at 13,000 rpm and the supernatant was collected for Western blot analysis. Samples were loaded onto a 10% poly-acrylamide gel and run at 125 volts. The protein was then transferred to a PVDF filter membrane (Immobilon-P, Millipore). An HRP-linked mouse CEA monoclonal antibody (1:1000; Fitzgerald) was used to detect the expression of mCEA with the enhancement from a chemiluminescence reagent (DNA Thunder™; NEN™ Life Science Products).

All six final CAP(6D)-1,2 recombinant white plaques (PRBC-III-2,3,6,8,9,10) and one intermediate blue plaque (pRBC-III-N1) showed only one CEA band with no other truncated form (FIG. 11). In contrast, protein from vCP307 plaques (recombinant ALVAC expressing native CEA) showed a clear truncated CEA product at ~60 kDa in addition to the full length CEA. Prolonged exposure of the film verified the absence of any truncated CEA polypeptides in the CAP(6D)-1,2 recombinants. CEF was used as the negative control.

In conclusion, the CAP(6D)-1,2 recombinants were generated with the mCEA instead of the native CEA to prevent the expression of multiple versions of CEA. CAP(6D)-1,2 expressed from recombinant NYVAC was proven effective in eliminating truncated version of CEA by both PCR and Western blot.

While the present invention has been described in terms of the preferred embodiments, it is understood that variations and modifications will occur to those skilled in the art. Therefore, it is intended that the appended claims cover all such equivalent variations that come within the scope of the invention as claimed.

The invention claimed is:

1. A method for preventing or treating a CEA antigen expressing cancer in a host comprising administering to the host an isolated expression vector comprising SEQ ID NO:28.

2. The method of claim 1 wherein the vector is a plasmid or a viral vector.

3. The method of claim 2 wherein the viral vector is selected from the group consisting of poxvirus, adenovirus, retrovirus, herpesvirus, and adeno-associated virus.

4. The method of claim 3 wherein the viral vector is a poxvirus selected from the group consisting of vaccinia, NYVAC, avipox, canarypox, ALVAC, ALVAC(2), fowlpox, and TROVAC.

5. The method of claim 1, wherein the expression vector further comprises a nucleic acid sequence encoding a co-stimulatory molecule.

6. The method of claim 5, wherein the co-stimulatory molecule is human B7.1.

7. The method of claim 1, wherein the expression vector further comprises a nucleic acid sequence encoding at least one additional tumor-associated antigen.

8. The method of claim 1, wherein the expression vector further comprises a nucleic acid sequence encoding at least one angiogenesis-associated antigen.

9. The method of claim 1 wherein the expression vector is admixed with a pharmaceutically acceptable carrier.

10. A method for preventing or treating a CEA antigen expressing cancer in a host comprising administering to the host an isolated expression vector comprising a CEA-encoding nucleic acid sequence including at least the sequence set forth by 421-1490 of SEQ ID NO:28.

11. The method of claim 10 wherein the vector is a plasmid or a viral vector.

12. The method of claim 11 wherein the viral vector is selected from the group consisting of poxvirus, adenovirus, retrovirus, herpesvirus, and adeno-associated virus.

13. The method of claim 12 wherein the viral vector is a poxvirus selected from the group consisting of vaccinia, NYVAC, avipox, canarypox, ALVAC, ALVAC(2), fowlpox, and TROVAC.

14. The method of claim 10, wherein the expression vector further comprises a nucleic acid sequence encoding a co-stimulatory molecule.

15. The method of claim 14, wherein the co-stimulatory molecule is human B7.1.

16. The method of claim 10, wherein the expression vector further comprises a nucleic acid sequence encoding at least one additional tumor-associated antigen.

17. The method of claim 10, wherein the expression vector further comprises a nucleic acid sequence encoding at least one angiogenesis-associated antigen.

18. The method of claim 10 wherein the expression vector is admixed with a pharmaceutically acceptable carrier.

* * * * *

SEQUENCE LISTING

<160> NUMBER OF SEQ ID NOS: 33

<210> SEQ ID NO 1
<211> LENGTH: 3564
<212> TYPE: DNA
<213> ORGANISM: Homo sapiens
<220> FEATURE:
<221> NAME/KEY: misc_feature
<222> LOCATION: (1663)..(1663)
<223> OTHER INFORMATION: n is a, c, g, or t

<400> SEQUENCE: 1

| | | | | | |
|---|---|---|---|---|---|
| agcaggaccg | gggcctgtgt | cgctatgggt | tcccccgccg | ccccggaggg | agcgctgggc | 60 |
| tacgtccgcg | agttcactcg | ccactcctcc | gacgtgctgg | gcaacctcaa | cgagctgcgc | 120 |
| ctgcgcggga | tcctcactga | cgtcacgctg | ctggttggcg | ggcaaccccct | cagagcacac | 180 |
| aaggcagttc | tcatcgcctg | cagtggcttc | ttctattcaa | ttttccgggg | ccgtgcggga | 240 |
| gtcggggtgg | acgtgctctc | tctgcccggg | ggtcccgaag | cgagaggctt | cgcccctcta | 300 |
| ttggacttca | tgtacacttc | gcgcctgcgc | ctctctccag | ccactgcacc | agcagtccta | 360 |
| gcggccgcca | cctatttgca | gatggagcac | gtggtccagg | catgccaccg | cttcatccag | 420 |
| gccagctatg | aacctctggg | catctcccctg | cgcccctgg | aagcagaacc | ccaacaccc | 480 |
| ccaacggccc | ctccaccagg | tagtcccagg | cgctccgaag | gacacccaga | cccacctact | 540 |
| gaatctcgaa | gctgcagtca | aggccccccc | agtccagcca | gccctgaccc | caaggcctgc | 600 |
| aactggaaaa | agtacaagta | catcgtgcta | aactctcagg | cctcccaagc | agggagcctg | 660 |
| gtcgggggaga | gaagttctgg | tcaaccttgc | ccccaagcca | ggctcccccag | tggagacgag | 720 |
| gcctccagca | gcagcagcag | cagcagcagc | agcagcagtg | aagaaggacc | cattcctggt | 780 |
| ccccagagca | ggctctctcc | aactgctgcc | actgtgcagt | tcaaatgtgg | ggctccagcc | 840 |
| agtaccccct | acctcctcac | atcccaggct | caagacacct | ctggatcacc | ctctgaacgg | 900 |
| gctcgtccac | taccgggagt | gaattttttca | gctgccagaa | ctgtgaggct | gtggcagggt | 960 |
| gctcatcggg | ggctggactc | cttggttcct | ggggacgaag | acaaacccta | taagtgtcag | 1020 |
| ctgtgccggt | cttcgttccg | ctacaagggc | aaccttgcca | gtcaccgtac | agtgcacaca | 1080 |
| ggggaaaagc | cttaccactg | ctcaatctgc | ggagcccgtt | taaccggcc | agcaaacctg | 1140 |
| aaaacgcaca | gccgcatcca | ttcgggagag | aagccgtata | agtgtgagac | gtgcggctcg | 1200 |
| cgctttgtac | aggtggcaca | tctgcgggcg | cacgtgctga | tccacaccgg | ggagaagccc | 1260 |
| taccccttgcc | ctacctgcgg | aacccgcttc | cgccacctgc | agaccctcaa | gagccacgtt | 1320 |
| cgcatccaca | ccggagagaa | gccttaccac | tgcgaccccct | gtggcctgca | tttccggcac | 1380 |
| aagagtcaac | tgcggctgca | tctgcgccag | aaaacacggag | ctgctaccaa | caccaaagtg | 1440 |
| cactaccaca | ttctcggggg | gcctagctg | agcgcaggcc | caggcccccac | ttgcttcctg | 1500 |
| cgggtgggaa | agctgcaggc | ccaggccttg | cttccctatc | aggcttgggc | ataggggtgt | 1560 |
| gccaggccac | tttggtatca | gaaattgcca | ccctcttaat | ttctcactgg | ggagagcagg | 1620 |
| ggtggcagat | cctggctaga | tctgcctctg | ttttgctggt | canaccctct | tccccacaag | 1680 |
| ccagattgtt | tctgaggaga | gagctagcta | ggggctggga | aaggggagag | attggagtcc | 1740 |
| tggtctccct | aagggaatag | ccctccacct | gtggcccccca | ttgcattcag | tttatctgta | 1800 |
| aaatataatt | tattgaggcc | tttgggtggc | accggggcct | tcattcgatt | gcatttccca | 1860 |
| ctcccctctt | ccacaagtgt | gattaaaagt | gaccagaaac | acagaaggtg | agatcacagc | 1920 |

-continued

```
tctgctggca gagattacta gcccttggct ctctcgtttg gcttgggtat tttatattat    1980
ttctgtcata acttttatct ttagaattgt tctttctcct gtttgtttgc ttgttagttt    2040
gtttaaaatg gaaaaggggg ttctctgtgt tctgcccctg taattctagg tctggaacct    2100
ttatttgttc tagggcagct ctgggaacat gcgggattgt ggaattgggt caggaaccct    2160
ctctggtatt ctggatgttg taggttctct agcagtctag aaatggatac agacatttct    2220
ctgttcttca agggtgatag gaaccattat gttgagccca aaatggaagt aataataaat    2280
gcctcctgga ggctgtgggt gtggggggatt ctgtatctgg attccgtatc actccaactg    2340
gaggctgtgg gtgtggggga ttctgtatct ggattccgta tcactccaag tggaggctgg    2400
caggtttttc tgcaagatgg tccagaatct aaaatgtccc attaatctgg tcacttgggt    2460
ttggctctgc tgtatccatc tatagtggta gagacccacc agggctcaag tggagtccat    2520
catcctccca cgggggcctg ttcttagtac tgagttgatc gctccatggg ggagagatca    2580
gacattcctt atcagagatg atgtgacctt ttctgactct gcccagtctc tatgaatgtt    2640
atggcctagg gaagaatcat gaaactcttt agcttgatta gatggtaaac agtgttaacc    2700
catcctttac tacagaggca tatgggtttg aatgttacct ggggttctct ctattgagtt    2760
gagccccttc ttcctttagt gggttttgga catcttctgg caagtgtcca gatgccagaa    2820
ccttcttttc tctagaagg gatggtgctt ggtaacctta ccttttaaaa gctgggtctg    2880
tgacctggtc ttcccatccc tgcattcctg tctggaacca gtgaatgcat tagaaccttc    2940
cataggaaaa gaaagggggc tgagttccat tctgggtttg ctgtagtttg gttgggatta    3000
ttgttggcat tacagatgta aaagattgac tagcccatag gccaaaggcc tgttctagtt    3060
gaccaagttt caagtaggat taagaggttg gttgaggggt gcagtttctg gtgtaggcca    3120
ggtaggtaga aagtgaggaa cagggttgcc tcttggctgg gtggagtctc tgaaatgtta    3180
gaagaagcgc tgaagccttg attgatagtt ctgcccttg ttgccctggg gcttatctga    3240
ttatgggacg agggtagaaa gtaagaagca cttttgaatt tgtggggtag aacttcaaca    3300
ataagtcagt tctagtggct gtcgcctggg gactagtgag aaagctactc ttctcccctct    3360 tccctctttc tccccatggc cccactgcag aattaaagaa ggaagaaggg aaggcggagg    3420
agtctataag aaggaatcat gatttctatt tagcagattg gatgggcagg tggagaatgc    3480
ctgggggtag aaatgttaga tcttgcaaca tcagatcctt ggaataaaga agcctctctg    3540
cgcaaaaaaa aaaaaaaaa aaaa                                            3564
```

<210> SEQ ID NO 2
<211> LENGTH: 1440
<212> TYPE: DNA
<213> ORGANISM: Homo sapiens

<400> SEQUENCE: 2

```
atgggttccc ccgccgcccc ggagggagcg ctgggctacg tccgcgagtt cactcgccac      60
tcctccgacg tgctgggcaa cctcaacgag ctgcgcctgc gcggatcct cactgacgtc     120 acgctgctgg ttggcgggca acccctcaga gcacacaagg cagttctcat cgcctgcagt     180
ggcttcttct attcaatttt ccggggccgt gcgggagtcg ggtggacgt gctctctctg     240 cccgggggtc ccgaagcgag aggcttcgcc cctctattgg acttcatgta cacttcgcgc     300
ctgcgcctct ctccagccac tgcaccagca gtcctagcgg ccgccaccta tttgcagatg     360
gagcacgtgg tccaggcatg ccaccgcttc atccaggcca gctatgaacc tctgggcatc     420
tccctgcgcc cctggaagc agaacccca acacccccaa cggcccctcc accaggtagt     480
```

-continued

```
cccaggcgct ccgaaggaca cccagaccca cctactgaat ctcgaagctg cagtcaaggc    540
ccccccagtc cagccagccc tgaccccaag gcctgcaact ggaaaaagta caagtacatc    600
gtgctaaact ctcaggcctc caagcaggg agcctggtcg gggagagaag ttctggtcaa     660
ccttgccccc aagccaggct ccccagtgga gacgaggcct ccagcagcag cagcagcagc    720
agcagcagca gtgaagaagg acccattcct ggtccccaga gcaggctctc tccaactgct    780
gccactgtgc agttcaaatg tggggctcca gccagtaccc cctacctcct cacatcccag    840
gctcaagaca cctctggatc accctctgaa cgggctcgtc cactaccggg aagtgaattt    900
ttcagctgcc agaactgtga ggctgtggca gggtgctcat cggggctgga ctccttggtt    960
cctggggacg aagacaaacc ctataagtgt cagctgtgcc ggtcttcgtt ccgctacaag   1020
ggcaaccttg ccagtcatcg tacagtgcac acagggaaa agccttacca ctgctcaatc    1080
tgcggagccc gttttaaccg gccagcaaac ctgaaaacgc acagccgcat ccattcggga   1140
gagaagccgt ataagtgtga cacgtgcggc tcgcgctttg tacaggtggc acatctgcgg   1200
gcgcacgtgc tgatccacac cggggagaag ccctacccct tgccctacct cggaaccccgc 1260 ttccgccacc tgcagaccct caagagccac gttcgcatcc acaccggaga gaagccttac   1320
cactgcgacc cctgtggcct gcatttccgg cacaagagtc aactgcggct gcatctgcgc   1380
cagaaacacg gagctgctac caacaccaaa gtgcactacc acattctcgg ggggccctag   1440

<210> SEQ ID NO 3
<211> LENGTH: 65
<212> TYPE: DNA
<213> ORGANISM: Homo sapiens

<400> SEQUENCE: 3
atacccggaa ctccctaagc cttctattag ctccaataat agtaagcctg tcgaagacaa     60
agatg                                                                65

<210> SEQ ID NO 4
<211> LENGTH: 70
<212> TYPE: DNA
<213> ORGANISM: Homo sapiens

<400> SEQUENCE: 4
gcctgtgtcc cctagactcc aactcagcaa cggaaataga actctgaccc tgtttaacgt     60
gaccaggaac                                                           70

<210> SEQ ID NO 5
<211> LENGTH: 70
<212> TYPE: DNA
<213> ORGANISM: Homo sapiens

<400> SEQUENCE: 5
acgtgcttta cggacccgat gctcctacaa tcagccctct aaacacaagc tatagatcag     60
gggaaaatct                                                           70

<210> SEQ ID NO 6
<211> LENGTH: 70
<212> TYPE: DNA
<213> ORGANISM: Homo sapiens

<400> SEQUENCE: 6
acgttaaaca gggtcagagt tctatttccg ttgctgagtt ggagtctagg ggacacaggc     60
agggactggt                                                           70
```

<210> SEQ ID NO 7
<211> LENGTH: 70
<212> TYPE: DNA
<213> ORGANISM: Homo sapiens

<400> SEQUENCE: 7
ctgatctata gcttgtgttt agagggctga ttgtaggagc atcgggtccg taaagcacgt    60
tgagaatcac                                                          70

<210> SEQ ID NO 8
<211> LENGTH: 63
<212> TYPE: DNA
<213> ORGANISM: Homo sapiens

<400> SEQUENCE: 8
gatccactat tgttcacggt aatattggga atgaacagtt cctgggtgga ctgttggaaa    60
gtg                                                                 63

<210> SEQ ID NO 9
<211> LENGTH: 70
<212> TYPE: DNA
<213> ORGANISM: Homo sapiens

<400> SEQUENCE: 9
gacacagcaa gctacaaatg cgaaacccaa aatccagtca gcgccaggag gtctgattca    60
gtgattctca                                                          70

<210> SEQ ID NO 10
<211> LENGTH: 70
<212> TYPE: DNA
<213> ORGANISM: Homo sapiens

<400> SEQUENCE: 10
tgaatcagac ctcctggcgc tgactggatt ttgggtttcg catttgtagc ttgctgtgtc    60
gttcctggtc                                                          70

<210> SEQ ID NO 11
<211> LENGTH: 79
<212> TYPE: DNA
<213> ORGANISM: Homo sapiens

<400> SEQUENCE: 11
gatcctacac gtgccaagct cacaatagcg acaccggact caaccgcaca accgtgacga    60
cgattaccgt gtatgccga                                                79

<210> SEQ ID NO 12
<211> LENGTH: 70
<212> TYPE: DNA
<213> ORGANISM: Homo sapiens

<400> SEQUENCE: 12
catcctcaac tgggttagaa ttgttactag ttatgaatgg ttttggtggc tcggcataca    60
cggtaatcgt                                                          70

<210> SEQ ID NO 13
<211> LENGTH: 80
<212> TYPE: DNA
<213> ORGANISM: Homo sapiens

<400> SEQUENCE: 13

-continued

| ttctaaccca gttgaggatg aggacgcagt tgcattaact tgtgagccag agattcaaaa | 60 |
| taccacttat ttatggtggg | 80 |

<210> SEQ ID NO 14
<211> LENGTH: 80
<212> TYPE: DNA
<213> ORGANISM: Homo sapiens
<400> SEQUENCE: 14

| gtctaatgat aaccgcacat tgacactcct gtccgttact cgcaatgatg taggaccta | 60 |
| tgagtgtggc attcagaatg | 80 |

<210> SEQ ID NO 15
<211> LENGTH: 80
<212> TYPE: DNA
<213> ORGANISM: Homo sapiens
<400> SEQUENCE: 15

| tttgtatggc ccagacgacc caactatatc tccatcatac acctactacc gtcccggcgt | 60 |
| gaacttgagc ctttcttgcc | 80 |

<210> SEQ ID NO 16
<211> LENGTH: 80
<212> TYPE: DNA
<213> ORGANISM: Homo sapiens
<400> SEQUENCE: 16

| tgatggaaac attcagcagc atactcaaga gttatttata agcaacataa ctgagaagaa | 60 |
| cagcggactc tatacttgcc | 80 |

<210> SEQ ID NO 17
<211> LENGTH: 80
<212> TYPE: DNA
<213> ORGANISM: Homo sapiens
<400> SEQUENCE: 17

| taaaacaata actgtttccg cggagctgcc caagccctcc atctccagca acaactccaa | 60 |
| acccgtggag gacaaggatg | 80 |

<210> SEQ ID NO 18
<211> LENGTH: 80
<212> TYPE: DNA
<213> ORGANISM: Homo sapiens
<400> SEQUENCE: 18

| atgtgcggtt atcattagac aactgcaagc gtgggctaac cggcaaactt tggttattga | 60 |
| cccaccataa ataagtggta | 80 |

<210> SEQ ID NO 19
<211> LENGTH: 80
<212> TYPE: DNA
<213> ORGANISM: Homo sapiens
<400> SEQUENCE: 19

| ggtcgtctgg gccatacaaa acattaagga taacagggtc ggagtgatca acggataatt | 60 |
| cattctgaat gccacactca | 80 |

<210> SEQ ID NO 20
<211> LENGTH: 80
<212> TYPE: DNA

<213> ORGANISM: Homo sapiens

<400> SEQUENCE: 20

| gctgctgaat gtttccatca atcagccagg agtactgtgc aggggggttg gatgctgcat | 60 |
| ggcaagaaag gctcaagttc | 80 |

<210> SEQ ID NO 21
<211> LENGTH: 80
<212> TYPE: DNA
<213> ORGANISM: Homo sapiens

<400> SEQUENCE: 21

| cggaaacagt tattgtttta actgtagtcc tgctgtgacc actggctgag ttattggcct | 60 |
| ggcaagtata gagtccgctg | 80 |

<210> SEQ ID NO 22
<211> LENGTH: 47
<212> TYPE: DNA
<213> ORGANISM: Homo sapiens

<400> SEQUENCE: 22

| cctcaggttc acaggtgaag gccacagcat ccttgtcctc cacgggt | 47 |

<210> SEQ ID NO 23
<211> LENGTH: 2106
<212> TYPE: DNA
<213> ORGANISM: Homo sapiens

<400> SEQUENCE: 23

| atggagtctc cctcggcccc tccccacaga tggtgcatcc cctggcagag gctcctgctc | 60 |
| acagcctcac ttctaacctt ctggaacccg cccaccactg ccaagctcac tattgaatcc | 120 |
| acgccgttca atgtcgcaga ggggaaggag gtgcttctac ttgtccacaa tctgccccag | 180 |
| catcttttg gctacagctg gtacaaaggt gaaagagtgg atggcaaccg tcaaattata | 240 |
| ggatatgtaa taggaactca acaagctacc cagggcccg catacagtgg tcgagagata | 300 |
| atataccca atgcatccct gctgatccag aacatcatcc agaatgacac aggattctac | 360 |
| accctacacg tcataaagtc agatcttgtg aatgaagaag caactggcca gttccgggta | 420 |
| tacccggagc tgcccaagcc ctccatctcc agcaacaact ccaaacccgt ggaggacaag | 480 |
| gatgctgtgg ccttcacctg tgaacctgag actcaggacg caacctacct gtggtgggta | 540 |
| aacaatcaga gcctcccggt cagtcccagg ctgcagctgt ccaatggcaa caggaccctc | 600 |
| actctattca atgtcacaag aaatgacaca gcaagctaca atgtgaaac ccagaaccca | 660 |
| gtgagtgcca gcgcagtga ttcagtcatc ctgaatgtcc tctatggccc ggatgccccc | 720 |
| accatttccc ctctaaacac atcttacaga tcaggggaaa atctgaacct ctcctgccac | 780 |
| gcagcctcta ccccacctgc acagtactct tggtttgtca atgggacttt ccagcaatcc | 840 |
| acccaagagc tctttatccc caacatcact gtgaataata gtggatccta cgtgccaa | 900 |
| gcccataact cagacactgg cctcaatagg accacagtca cgacgatcac agtctatgag | 960 |
| ccacccaaac ccttcatcac cagcaacaac tccaaccccg tggaggatga ggatgctgta | 1020 |
| gccttaacct gtgaacctga gattcagaac acaacctacc tgtggtgggt aaataatcag | 1080 |
| agcctcccgg tcagtcccag gctgcagctg tccaatgaca caggaccct cactctactc | 1140 |
| agtgtcacaa ggaatgatgt aggacccat gagtgtggaa tccagaacga attaagtgtt | 1200 |
| gaccacagcg acccagtcat cctgaatgtc ctctatggcc cagacgaccc caccatttcc | 1260 |

-continued

```
ccctcataca cctattaccg tccaggggtg aacctcagcc tctcctgcca tgcagcctct    1320
aacccacctg cacagtattc ttggctgatt gatgggaaca tccagcaaca cacacaagag    1380
ctctttatct ccaacatcac tgagaagaac agcggactct atacctgcca ggccaataac    1440
tcagccagtg ccacagcag gactacagtc aagacaatca cagtctctgc ggagctgccc     1500
aagccctcca tctccagcaa caactccaaa cccgtggagg acaaggatgc tgtggccttc    1560
acctgtgaac ctgaggctca gaacacaacc tacctgtggt gggtaaatgg tcagagcctc    1620
ccagtcagtc ccaggctgca gctgtccaat ggcaacagga ccctcactct attcaatgtc    1680
acaagaaatg acgcaagagc ctatgtatgt ggaatccaga actcagtgag tgcaaaccgc    1740
agtgacccag tcaccctgga tgtcctctat gggccggaca cccccatcat ttccccccca    1800
gactcgtctt accttccggg agcggacctc aacctctcct gccactcggc ctctaaccca    1860
tccccgcagt attcttggcg tatcaatggg ataccgcagc aacacacaca agttctcttt    1920
atcgccaaaa tcacgccaaa taataacggg acctatgcct gttttgtctc taacttggct    1980
actggccgca ataattccat agtcaagagc atcacagtct ctgcatctgg aacttctcct    2040
ggtctctcag ctggggccac tgtcggcatc atgattggag tgctggttgg ggttgctctg    2100
atatag                                                                2106
```

<210> SEQ ID NO 24
<211> LENGTH: 47
<212> TYPE: DNA
<213> ORGANISM: Artificial sequence
<220> FEATURE:
<223> OTHER INFORMATION: Homo sapiens

<400> SEQUENCE: 24

```
ggacggtagt aggtgtatga tggagatata gttgggtcgt ctgggcc                  47
```

<210> SEQ ID NO 25
<211> LENGTH: 27
<212> TYPE: DNA
<213> ORGANISM: Artificial sequence
<220> FEATURE:
<223> OTHER INFORMATION: Homo sapiens

<400> SEQUENCE: 25

```
cagaatgaat tatccgttga tcactcc                                         27
```

<210> SEQ ID NO 26
<211> LENGTH: 45
<212> TYPE: DNA
<213> ORGANISM: Artificial sequence
<220> FEATURE:
<223> OTHER INFORMATION: Homo sapiens

<400> SEQUENCE: 26

```
cgtgacgacg attaccgtgt atgagccacc aaaaccattc ataac                     45
```

<210> SEQ ID NO 27
<211> LENGTH: 45
<212> TYPE: DNA
<213> ORGANISM: Artificial sequence
<220> FEATURE:
<223> OTHER INFORMATION: Homo sapiens

<400> SEQUENCE: 27

```
gttatgaatg gttttggtgg ctcatacacg gtaatcgtcg tcacg                     45
```

<210> SEQ ID NO 28

<211> LENGTH: 2106
<212> TYPE: DNA
<213> ORGANISM: Artificial sequence
<220> FEATURE:
<223> OTHER INFORMATION: Homo sapiens

<400> SEQUENCE: 28

| | | | | | |
|---|---|---|---|---|---|
| atggagtctc | cctcggcccc | tccccacaga | tggtgcatcc | cctggcagag | gctcctgctc | 60 |
| acagcctcac | ttctaacctt | ctggaacccg | cccaccactg | ccaagctcac | tattgaatcc | 120 |
| acgccgttca | atgtcgcaga | ggggaaggag | gtgcttctac | ttgtccacaa | tctgccccag | 180 |
| catcttttg | gctacagctg | gtacaaaggt | gaaagagtgg | atggcaaccg | tcaaattata | 240 |
| ggatatgtaa | taggaactca | acaagctacc | ccagggcccg | catacagtgg | tcgagagata | 300 |
| atataccccca | atgcatccct | gctgatccag | aacatcatcc | agaatgacac | aggattctac | 360 |
| accctacacg | tcataaagtc | agatcttgtg | aatgaagaag | caactggcca | gttccgggta | 420 |
| tacccggaac | tccctaagcc | ttctattagc | tccaataata | gtaagcctgt | cgaagacaaa | 480 |
| gatgccgtcg | cttttacatg | cgagcccgaa | actcaagacg | caacatatct | ctggtgggtg | 540 |
| aacaaccagt | ccctgcctgt | gtccctaga | ctccaactca | gcaacggaaa | tagaactctg | 600 |
| accctgttta | acgtgaccag | gaacgacaca | gcaagctaca | aatgcgaaac | ccaaaatcca | 660 |
| gtcagcgcca | ggaggtctga | ttcagtgatt | ctcaacgtgc | tttacggacc | cgatgctcct | 720 |
| acaatcagcc | ctctaaacac | aagctataga | tcaggggaaa | atctgaatct | gagctgtcat | 780 |
| gccgctagca | atcctcccgc | ccaatacagc | tggtttgtca | atggcacttt | ccaacagtcc | 840 |
| acccaggaac | tgttcattcc | caatattacc | gtgaacaata | gtggatccta | cacgtgccaa | 900 |
| gctcacaata | gcgacaccgg | actcaaccgc | acaaccgtga | cgacgattac | cgtgtatgag | 960 |
| ccaccaaaac | cattcataac | tagtaacaat | tctaacccag | ttgaggatga | ggacgcagtt | 1020 |
| gcattaactt | gtgagccaga | gattcaaaat | accacttatt | tatggtgggt | caataaccaa | 1080 |
| agtttgccgg | ttagcccacg | cttgcagttg | tctaatgata | accgcacatt | gacactcctg | 1140 |
| tccgttactc | gcaatgatgt | aggaccttat | gagtgtggca | ttcagaatga | attatccgtt | 1200 |
| gatcactccg | accctgttat | ccttaatgtt | ttgtatggcc | cagacgaccc | aactatatct | 1260 |
| ccatcataca | cctactaccg | tcccggcgtg | aacttgagcc | tttcttgcca | tgcagcatcc | 1320 |
| aaccccctg | cacagtactc | ctggctgatt | gatggaaaca | ttcagcagca | tactcaagag | 1380 |
| ttatttataa | gcaacataac | tgagaagaac | agcggactct | atacttgcca | ggccaataac | 1440 |
| tcagccagtg | gtcacagcag | gactacagtt | aaaacaataa | ctgtttccgc | ggagctgccc | 1500 |
| aagccctcca | tctccagcaa | caactccaaa | cccgtggagg | acaaggatgc | tgtggccttc | 1560 |
| acctgtgaac | ctgaggctca | gaacacaacc | tacctgtggt | gggtaaatgg | tcagagcctc | 1620 |
| ccagtcagtc | ccaggctgca | gctgtccaat | ggcaacagga | ccctcactct | attcaatgtc | 1680 |
| acaagaaatg | acgcaagagc | ctatgtatgt | ggaatccaga | actcagtgag | tgcaaaccgc | 1740 |
| agtgacccag | tcaccctgga | tgtcctctat | gggccggaca | cccccatcat | ttccccccca | 1800 |
| gactcgtctt | acctttcggg | agcggacctc | aacctctcct | gccactcggc | tctaacccca | 1860 |
| tccccgcagt | attcttggcg | tatcaatggg | ataccgcagc | aacacacaca | agttctcttt | 1920 |
| atcgccaaaa | tcacgccaaa | taataacggg | acctatgcct | gttttgtctc | taacttggct | 1980 |
| actggccgca | ataattccat | agtcaagagc | atcacagtct | ctgcatctgg | aacttctcct | 2040 |
| ggtctctcag | ctggggccac | tgtcggcatc | atgattggag | tgctggttgg | ggttgctctg | 2100 |
| atatag | | | | | | 2106 |

```
<210> SEQ ID NO 29
<211> LENGTH: 35
<212> TYPE: DNA
<213> ORGANISM: Artificial sequence
<220> FEATURE:
<223> OTHER INFORMATION: Homo sapiens

<400> SEQUENCE: 29
ctggcgcgcc ttctttattc tatacttaaa aagtg                              35

<210> SEQ ID NO 30
<211> LENGTH: 36
<212> TYPE: DNA
<213> ORGANISM: Artificial sequence
<220> FEATURE:
<223> OTHER INFORMATION: Homo sapiens

<400> SEQUENCE: 30
ctggtaccag aaaaactata tcagagcaac cccaac                             36

<210> SEQ ID NO 31
<211> LENGTH: 26
<212> TYPE: DNA
<213> ORGANISM: Artificial sequence
<220> FEATURE:
<223> OTHER INFORMATION: Homo sapiens

<400> SEQUENCE: 31
ttggatccat ggagtctccc tcggcc                                        26

<210> SEQ ID NO 32
<211> LENGTH: 26
<212> TYPE: DNA
<213> ORGANISM: Artificial sequence
<220> FEATURE:
<223> OTHER INFORMATION: Homo sapiens

<400> SEQUENCE: 32
ttggatccct atatcagagc aacccc                                        26

<210> SEQ ID NO 33
<211> LENGTH: 16
<212> TYPE: PRT
<213> ORGANISM: Homo sapiens

<400> SEQUENCE: 33

Ser Arg Arg His His Cys Arg Ser Lys Ala Lys Arg Ser Arg His His
1               5                   10                  15
```